(12) United States Patent
Kirkegaard et al.

(10) Patent No.: US 7,476,499 B2
(45) Date of Patent: Jan. 13, 2009

(54) METHODS OF IDENTIFYING ANTI-VIRAL AGENTS

(75) Inventors: Karla A. Kirkegaard, Palo Alto, CA (US); Scott M. Crowder, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 7 days.

(21) Appl. No.: 11/762,607

(22) Filed: Jun. 13, 2007

(65) Prior Publication Data

US 2008/0090225 A1    Apr. 17, 2008

Related U.S. Application Data

(60) Provisional application No. 60/814,229, filed on Jun. 16, 2006.

(51) Int. Cl.
*C12Q 1/70* (2006.01)
*C12Q 1/18* (2006.01)

(52) U.S. Cl. .................................. 435/5; 435/6; 435/7.1

(58) Field of Classification Search .................. None
See application file for complete search history.

(56) References Cited

OTHER PUBLICATIONS

Crowder et al., (2005) Trans-dominant inhibition of RNA viral replication can slow growth of drug-resistant viruses, Nature Genetics, vol. 37, No. 7, pp. 701-709.
Herskowitz (1987), Functional inactivation of genes by dominant negative mutations, *Nature*, vol. 329, pp. 219-222.

*Primary Examiner*—Bruce Campell
*Assistant Examiner*—Michelle Horning
(74) *Attorney, Agent, or Firm*—Paula A. Borden; Bozicevic, Field & Francis LLP

(57) ABSTRACT

The present invention provides methods of identifying candidate anti-viral agents.

11 Claims, 15 Drawing Sheets

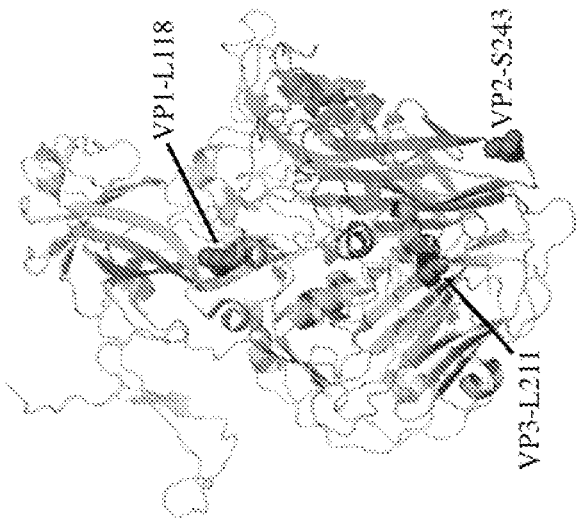
FIG. 1A
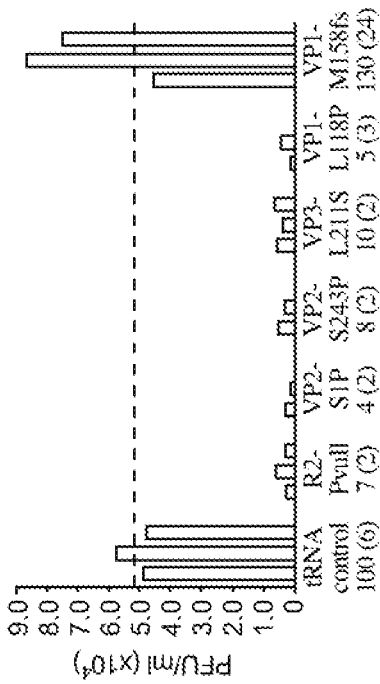
FIG. 1B
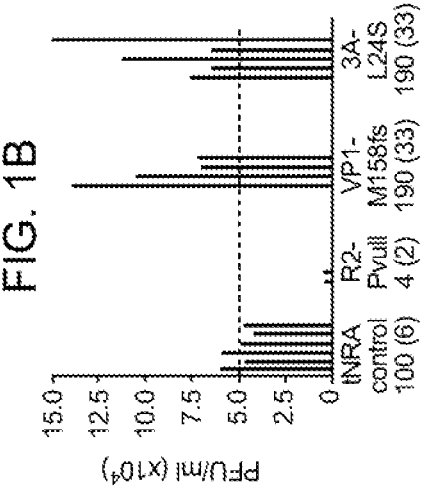
FIG. 1C
FIG. 1D

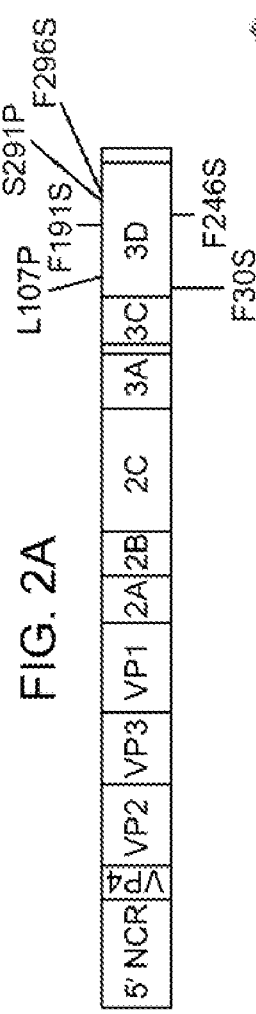
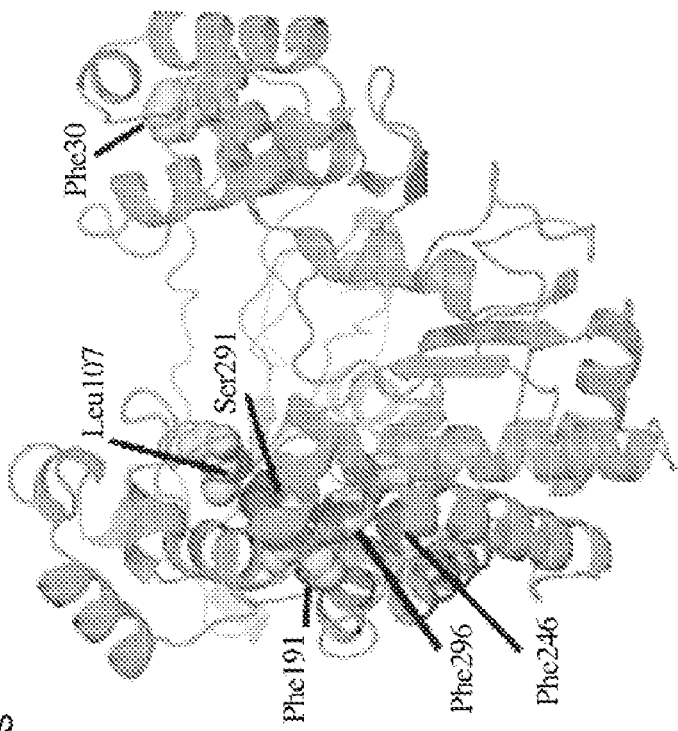
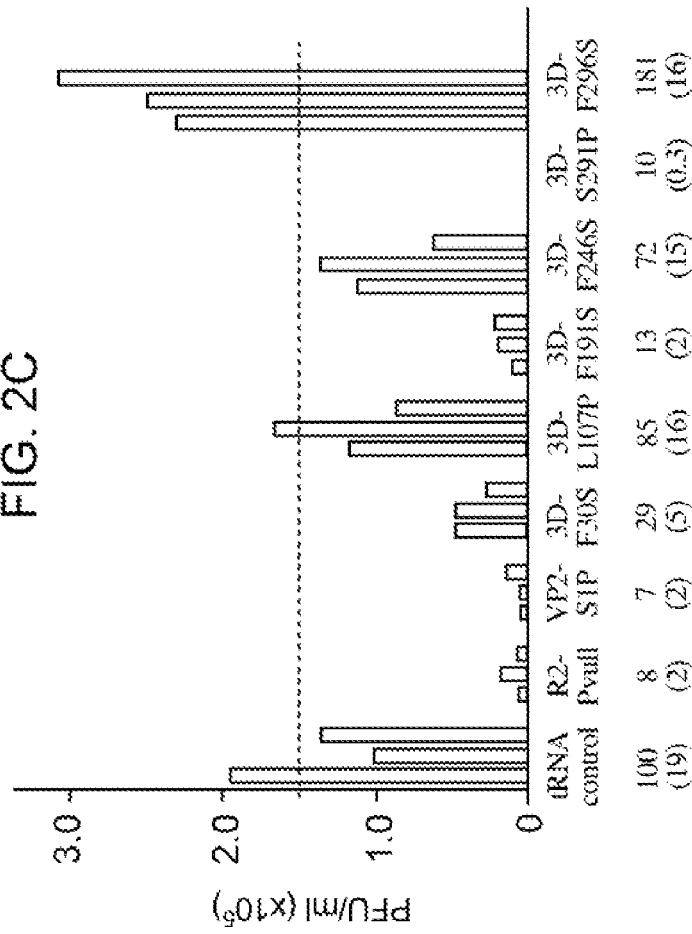
FIG. 2A
FIG. 2B
FIG. 2C

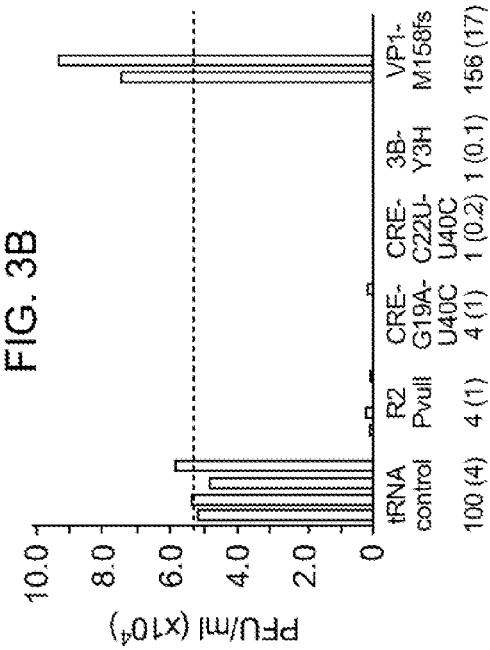
FIG. 3A
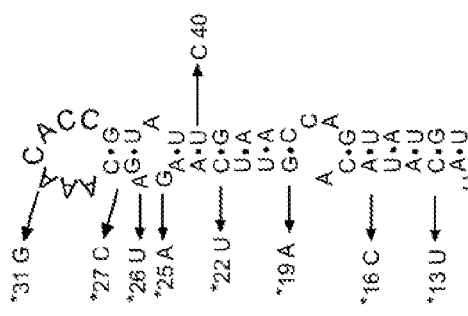
FIG. 3B
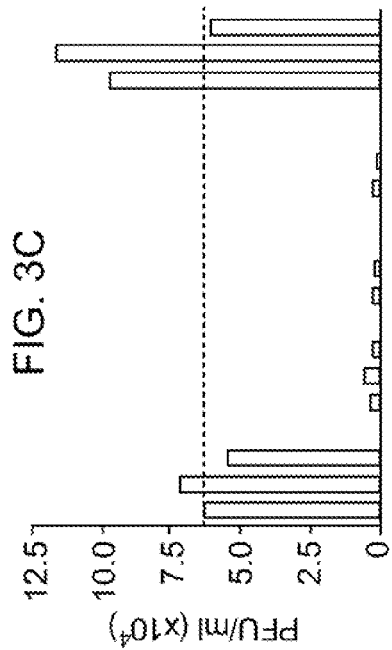
FIG. 3C
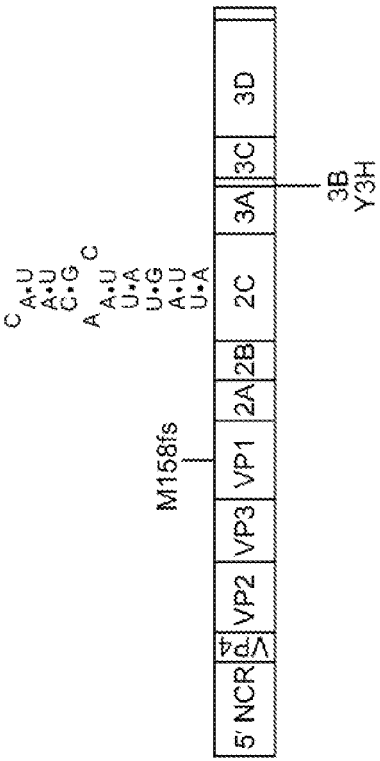

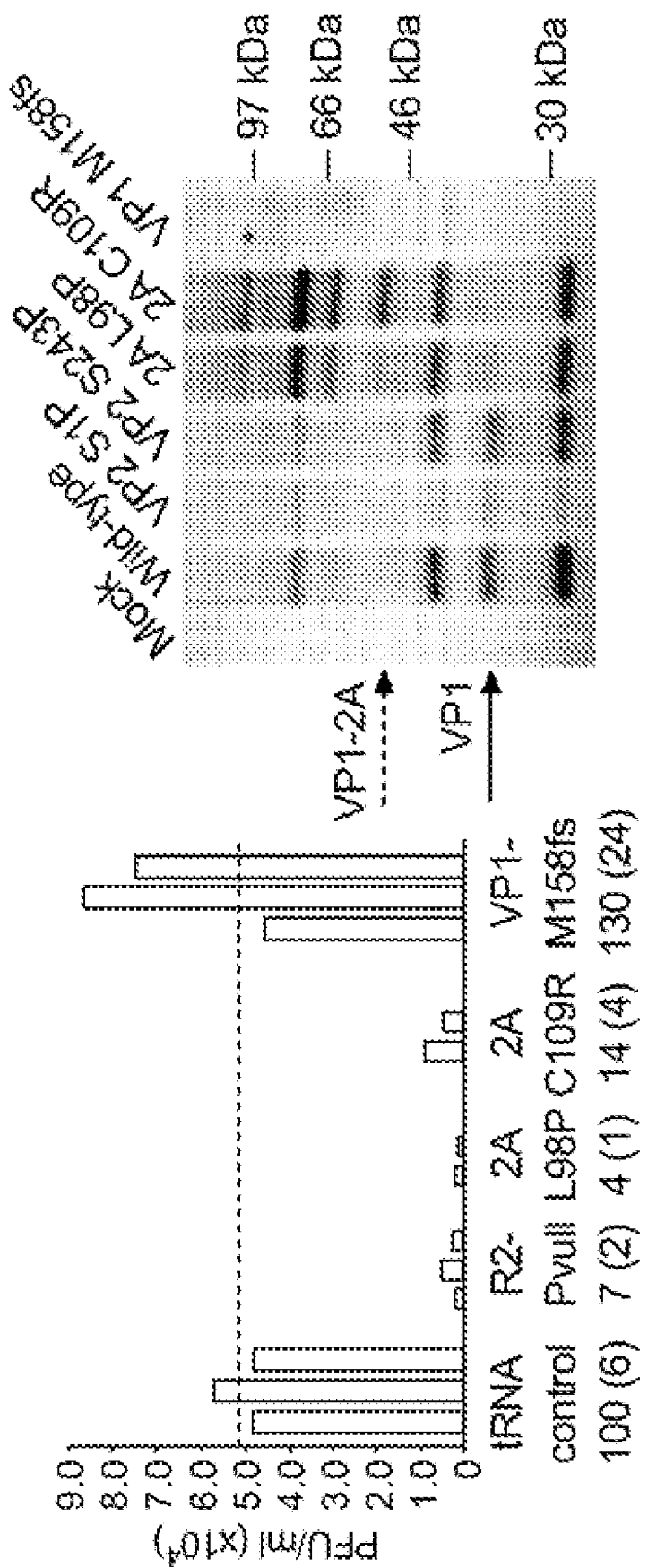

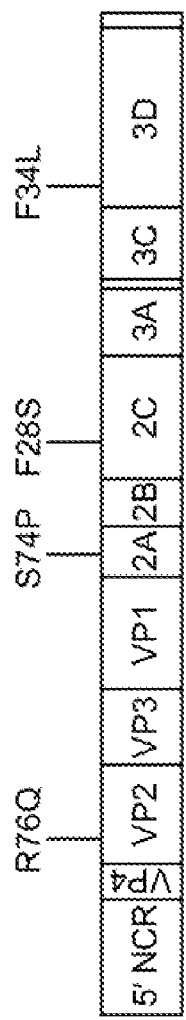
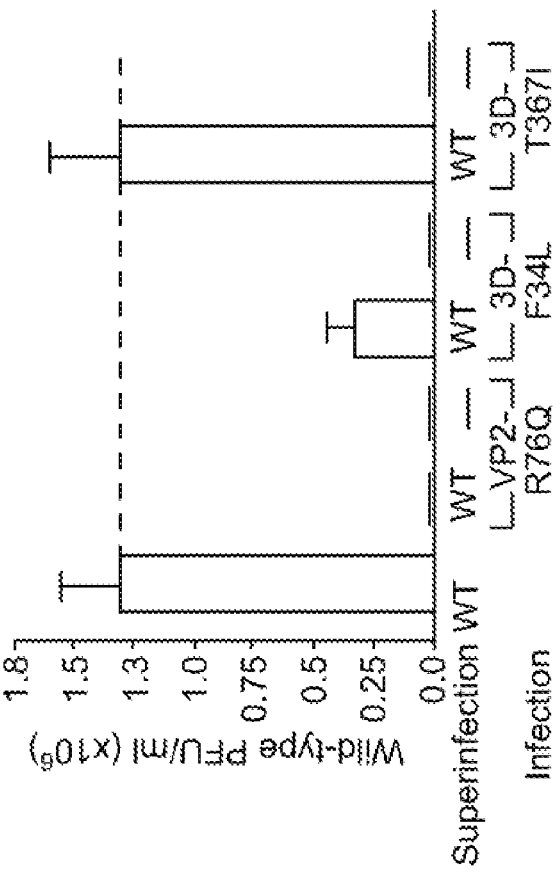
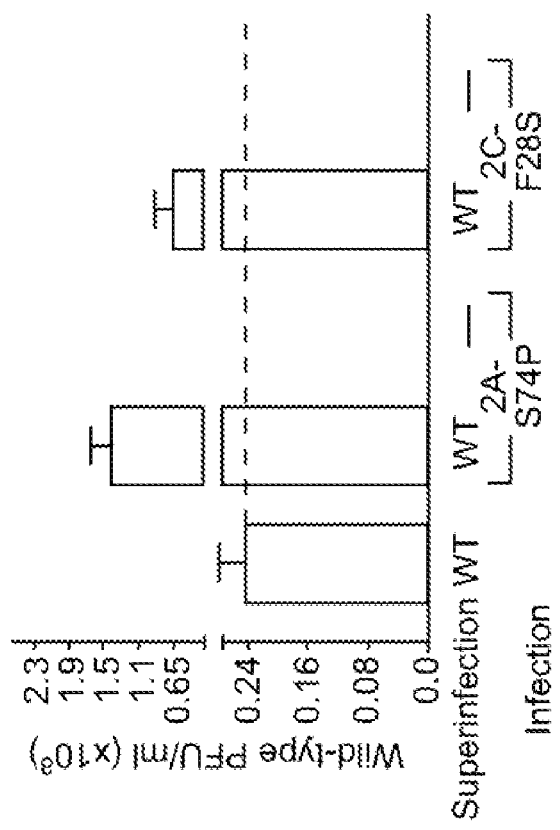
FIG. 6A
FIG. 6B
FIG. 6C

FIG. 9

GenBank NP_740469

```
  1 spnieacgys drvlqltlgn stittqeaan svvaygrwpe ylrdseanpv dqptepdvas
 61 crfytldtvs wtkesrqwww klpdalrdmg lfggnmyyhy lgrsgytvnv qenaskfbqg
121 algvfavpem clagdsnttt mhtsyqnasp gekggtftgt ftpdnnqtsp arsfcpvdyl
181 lynqtllqna fvfphqiinl rtnncatlvl pyvnslsids mvkhnnwqia ilplsplnfs
241 sesspeipit ltiapmccef nglrnitlpr lq (SEQ ID NO:3)
```

FIG. 10

GenBank NP_740470

```
  1 glpvxntpgs nqyltadnfq spcalpsfdv tppidipgev knmmelaeid tmipfdlsat
 61 kkntmemyrv rlsdkpntdd pilclslspa sdprlshtml qeilnyythw eqslkftflf
121 cgfmmatgkl lvsyappgad ppkkrkeaml qthviwdigl qssctmvvpw isnttyrqti
181 ddsfteggyi svfyqtrivv plstpremdi lgfvsacndf svrlirdtth ieqkalaq
(SEQ ID NO:4)
```

FIG. 11

GenBank NP_740471

```
  1 glgqmlesmi dntvretvga atsrdalpst easqpthske ipaltavetg atnplvpsdt
 61 vqtshvvqhr srsessiesf farqacvtim tvdapasttn kdklfavwki tykdtvqlrr
121 klefftysrf dmeltfvvta nftetsngha lnqvyqimyv ppgapvpekw ddytwqtssn
181 psifytygta parisvpyvq isnayshfyd gfskvplkdq ssalgdslyg aasindfgil
241 avrvvndhnp tkvtskirvy lkpkhirvwc prppravayy gpgvdykdgt ltplstkdlt
301 ty (SEQ ID NO:5)
```

FIG. 12

GenBank NP_740477

```
  1 gfqhqnkavy tagyklcnyh latqddlqna vnvmwsrdll vtesraqgtd siarcncneq
 61 vyycesrrky ypvsfvgptf qymeannyyp aryqshmlig hgfaspgdcg gilrchhgvi
121 glitaggegl vafsdirdly ayeeeameq (SEQ ID NO:6)
```

FIG. 13

GenBank NP_740472

```
  1 qitnyieslg aafgsgftqq isdkiteitn mvtstitekl lknlikiiss lviitrnyed
 61 tttvlatlal lgcdaspwqv lrkkacdvle ipyvikq (SEQ ID NO:7)
```

FIG. 14

GenBank NP_740473

```
  1 gdswlkkfte acnaakylew vankiskfid wltekiipqa rdklefvtkl rqlemlenqi
 61 stihqscpsq ehqeilfnmv rvlsiqskrf aplyaveakr iqklehtinn yiqfkskhri
121 epvcllvhqs pgtgksvatn liaraiaere ntstyslppd pshfdqykqg gvvimddlnq
181 npdgadmklf cqmvstvefi ppmasleekg ilftsnyvla stussrispp tvahsdalar
241 rfaidmdiqv mneysrdgkl nmamatemck nchqpanfkr ccplvcgkai qlmdksservr
301 ysidqittmi inesrnrrsni qncmealfq (SEQ ID NO:8)
```

FIG. 15

GenBank NP_740474

```
  1 gplqykdlki diktspppec indllqavds qevrdycekk gsivnitsqv qternisram
 61 tilqavttfa avagvvyvmy klfaghq (SEQ ID NO:9)
```

FIG. 16

GenBank NP_740475

```
1 gaytgipnkk pnvptirtak vq (SEQ ID NO:10)
```

FIG. 17

GenBank NP_740476

```
  1 gpgfdyavam akrnivtstt skgeftmlgv hdnvailpth aspgesivid gkeveiidak
 61 aledqagtnl eitiitlkrn ekirdirphi ptqitetndg vlivstskyp nmyvpvgavt
121 eggyinlggr qtartlmynf ptragqcggv itotgkvigm hvgqngshgf aaaikrsyft
181 qsq (SEQ ID NO:11)
```

FIG. 18

GenBank NP_740478

```
  1 qeiqwmrpsk evgypiinap sktklepsaf hyvfegvkep avltkndprl ktdfeeaifs
 61 kyvgskitev deymkeavdh yagqimsldi nteqmoleda mygtdglsal distsagypy
121 vamqkkkrdi lnkqtrdtke mgklidtygi nlpivtyvkd elrsktkveq gksrlieass
181 lndsvamzma fgnlyaafhk spgvitgsav qcdpdlfwsk ipvlmeeklf afdytgydas
241 lspawfealk mvlekigfqd rvdyldylsh shhlyknkty cvkggmpsgc sgtsifnsmi
301 anliirtlli ktykqidldh lkmiaygddv iasyphevda allaqsqkdy qltmtpadks
361 atfetvtwen vtflkrffra dekypflihp vmpmkeihes irwtkdprnt qdhvrslcll
421 awhngeeeyn kflakirsvp igraillpey stlyrrwids f (SEQ ID NO:12)
```

FIG. 19

GenBank NP_740468

```
  1 gaqvssqkvg ahenenrayg gstinyttin yyrdsasnaa skqdfsqdps kftepikdvl
 61 iktapmln (SEQ ID NO:13)
```

METHODS OF IDENTIFYING ANTI-VIRAL AGENTS

CROSS-REFERENCE

This application claims the benefit of U.S. Provisional Patent Application No. 60/814,229, filed Jun. 16, 2006, which application is incorporated herein by reference in its entirety.

STATEMENT REGARDING FEDERALLY SPONSORED RESEARCH

This invention was made with government support under contact F32A150296 awarded by the National Institutes of Health. The Government has certain rights in this invention.

BACKGROUND

The error-prone replication of RNA viral genomes makes them notorious for their ability to evolve resistance to selective agents rapidly and effectively. For cytoplasmic positive-strand RNA viruses such as poliovirus, other picornaviruses such as foot-and-mouth disease virus, and more distantly related flaviviruses such as Dengue and West Nile viruses, an infection started by a single genome can quickly become heterogeneous, even in the first infected cell. Therefore, a progeny genome containing a newly generated mutation that could confer a selective advantage must replicate and package in the context of an essentially polyploid infection in order to propagate.

There is a need in the art for anti-viral agents that, when administered, do not give rise to drug-resistant virus in the early stages of viral infection.

Literature

Herskowitz (1987) *Nature* 329:219-222; Crowder and Kirkegaard (2005 July) *Nat. Genet.* 37(7):701-9 (Epub 2005 Jun. 19).

SUMMARY OF THE INVENTION

The present invention provides methods of identifying candidate anti-viral agents.

BRIEF DESCRIPTION OF THE DRAWINGS

FIGS. 1A-D depict a dominant inhibitor screen for capsid-coding genome regions.

FIGS. 2A-C depict the effect of mutations in 3D polymerase on the yield of wild-type virus during co-transfection.

FIGS. 3A-C depict a dominant inhibitor screen in the CRE and 3B-coding regions.

FIGS. 4A-E depict a dominant inhibitor screen for 2A proteinase and VP1-2A cleavage site mutant alleles.

FIGS. 6A-C depict superinfections of wild-type and temperature-sensitive polioviruses.

FIGS. 7A-E depict co-infections of drug-sensitive and drug-resistant viruses.

FIG. 8 is a schematic depiction of an exemplary assay.

FIGS. 9-19 provide amino acid sequences of poliovirus type 1 (Mahoney) proteins VP2, VP3, VP1, 2A, 2B, 2C, 3A, 3B, 3C, 3D, and VP4, respectively.

DEFINITIONS

The terms "polynucleotide" and "nucleic acid", used interchangeably herein, refer to a polymeric forms of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "oligopeptide," "polypeptide," "polyprotein," and "protein" are used interchangeably herein, and refer to a polymeric form of amino acids of any length, which can include coded and non-coded amino acids, chemically or biochemically modified or derivatized amino acids, and polypeptides having modified peptide backbones.

"Recombinant," as used herein, means that a particular DNA sequence is the product of various combinations of cloning, restriction, and/or ligation steps resulting in a construct having a structural coding sequence distinguishable from homologous sequences found in natural systems. Generally, DNA sequences encoding the structural coding sequence can be assembled from cDNA fragments and short oligonucleotide linkers, or from a series of oligonucleotides, to provide a synthetic gene which is capable of being expressed in a recombinant transcriptional unit. Such sequences can be provided in the form of an open reading frame uninterrupted by internal nontranslated sequences, or introns, which are typically present in eukaryotic genes. Genomic DNA comprising the relevant sequences could also be used. Sequences of non-translated DNA may be present 5' or 3' from the open reading frame, where such sequences do not interfere with manipulation or expression of the coding regions. Thus, e.g., the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

By "construct" is meant a recombinant nucleic acid, generally recombinant DNA, that has been generated for the purpose of the expression of a specific nucleotide sequence(s), or is to be used in the construction of other recombinant nucleotide sequences.

Similarly, a "recombinant polypeptide" or "recombinant polyprotein" refers to a polypeptide or polyprotein which is not naturally occurring, or is made by the artificial combination of two otherwise separated segments of amino acid sequences. This artificial combination may be accomplished by standard techniques of recombinant DNA technology, such as described above, i.e., a recombinant polypeptide or recombinant polyprotein may be encoded by a recombinant polynucleotide. Thus, a recombinant polypeptide or recombinant polyprotein is an amino acid sequence encoded by all or a portion of a recombinant polynucleotide.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Figure 4B:
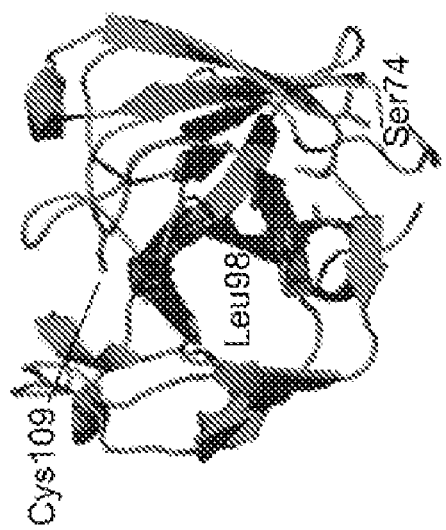

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an RNA virus" includes a plurality of such viruses and reference to "the anti-viral agent" includes reference to one or more anti-viral agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods of identifying candidate anti-viral agents. The invention is based at least on part on the discovery that choices of anti-viral drug target can be made so that drug-sensitive viral genomes dominantly inhibit the outgrowth of drug-resistant viral genomes in a cell. The ability of relatively unfit viruses to inhibit growth of viruses with increased fitness derives from, for example, the intracellular amplification of positive-strand RNA-viral genomes, their translation into large polyproteins, and the higher-order oligomerization of several of their protein products.

Accordingly, the invention is based in part on the concept that certain viral products, when defective, can dominantly interfere with growth of non-defective viruses, making these viral products good drug targets. Interaction of an anti-viral drug with a viral product essentially renders that viral product "defective" in function. Thus, if a viral product that, when defective due to mutation or drug interaction, is targeted by an anti-viral drug, then upon such viral products will dominantly interfere with other viruses in the cells in the presence of the drug. Stated differently, if defects similar to those introduced by a dominant mutations can be mimicked by antiviral drugs, the defective drug-sensitive viral genomes and products will dominantly interfere with the intracellular growth of any resistant mutant genomes that might arise.

Accordingly, drug sensitive viruses (i.e., viruses that produce a viral drug target that, upon drug interaction, dominantly interferes with other viruses) will be dominant over drug-resistant variants which contain a mutation in the targeted viral product. Therefore, as mutant, drug-resistant viruses arise in the cell, the presence of other viruses in the same cell that are still drug-sensitive will inhibit the growth of the drug-resistant virus. As such, this strategy will at least delay the emergence of drug-resistant viruses. This concept was borne out in experiments conducted with poliovirus, a positive-strand RNA virus.

Suitable drug targets were identified by introducing mutations into the poliovirus genome, generating variant, non-viable poliovirus, a number of which encoded variant viral protein. Mammalian cells were cultured in vitro, where the cells included both parent poliovirus and variant poliovirus. A number of variant poliovirus that interfered with growth of the parent poliovirus in the cell were identified, and the mutations in the genomes of the variant poliovirus were identified. Mutations giving rise to the growth-interfering phenotype included mutations within the capsid coding region; mutations in the polymerase coding region; mutations in the protein primer 3B coding region and in the cis-acting replication element; and mutations in the 2A proteinase coding region. Because the variant proteins and/or RNAs interfered with growth of parent poliovirus, they were referred to as "dominant targets." A dominant target would be a RNA or protein target that, when defective, dominantly interferes with the growth of non-defective virus.

Figure 8:
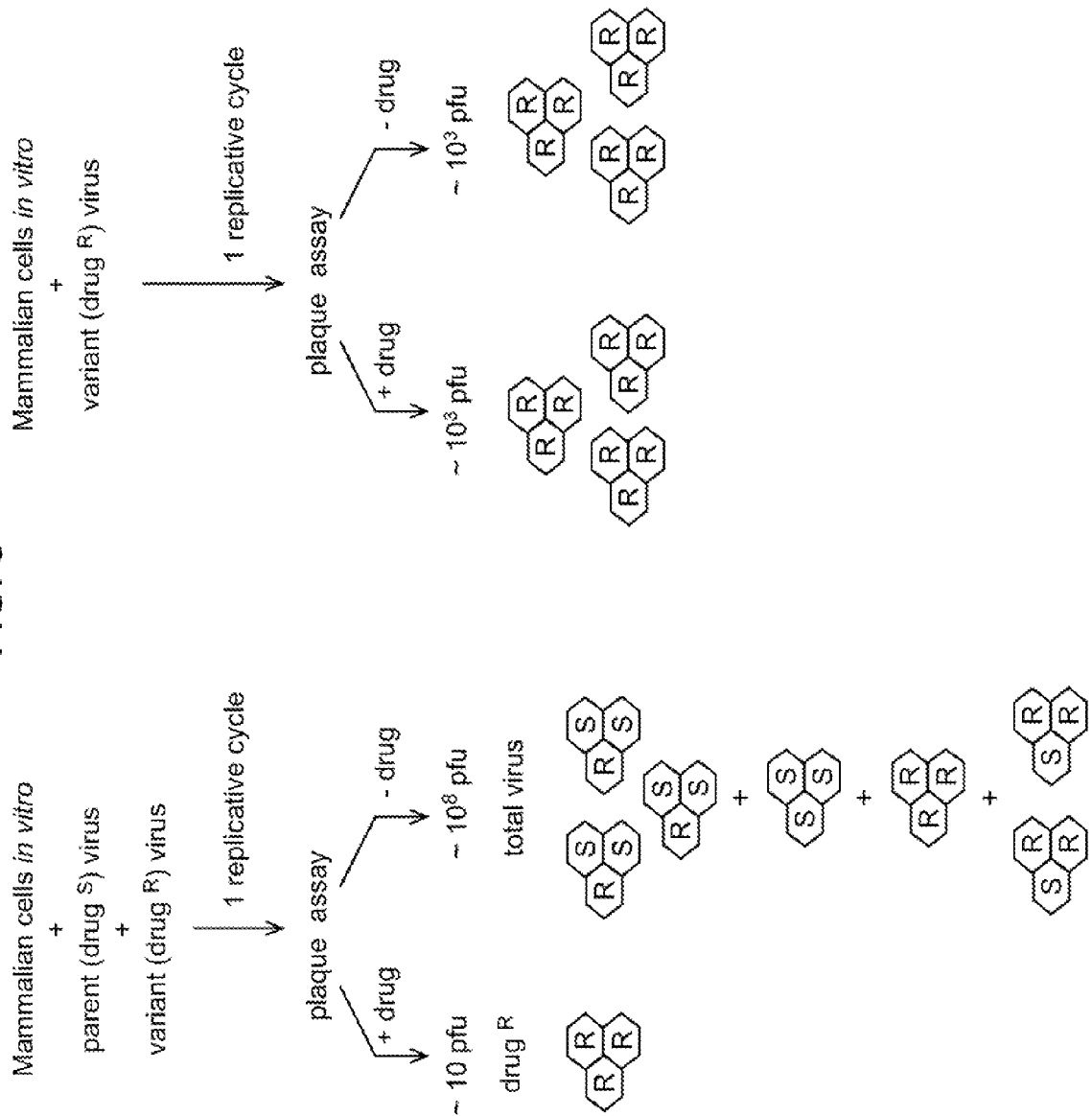

It was also observed that the presence of a drug-sensitive virus inhibits growth of a drug-resistant virus in a cell in the presence of the drug, where the drug target is a dominant viral protein. FIG. 8 provides a schematic depiction of an exemplary assay for the effect of growth of a parent, drug-sensitive virus on growth of a variant, drug-resistant virus.

The present invention provides methods for identifying a candidate anti-viral agent, where the emergence of drug-resistant virus in an individual following administration of such an agent is reduced or delayed. A delay in emergence of drug-resistant virus allows an individual to mount an effective immune response to the virus. Thus, the individual can clear the infection before emergence of drug-resistant virus.

Methods of Identifying Candidate Anti-Viral Agents

The present invention provides methods of identifying a candidate anti-viral agent. The methods generally involve:

a) culturing a mammalian cell in vitro, where the mammalian cell comprises: i) a parent RNA virus, where growth of the parent RNA virus is inhibited by a test agent; and ii) a variant of the parent RNA virus, where growth of the variant RNA virus is resistant to the test agent; and b) determining the effect, if any, of parent virus growth on growth of the variant virus during at least one replicative cycle.

If parent virus growth interferes with the variant virus growth during at least one replicative cycle, the test agent is considered a candidate anti-viral agent. In some embodiments, the parent virus growth interferes with growth of the variant virus during one replicative cycle in vitro or in vivo. In other embodiments, the parent virus growth interferes with growth of the variant virus during two, three, four, five, six, seven, eight, nine, ten, or more, replicative cycles in vitro or in vivo. Mammalian cells cultured in vitro and comprising both parent RNA virus and variant RNA virus, e.g., step (a), can be cultured in the presence or absence of the test agent. In some embodiments, step (a) is carried out in the absence of test agent.

A replicative cycle varies from virus to virus; replicative cycles for various RNA viruses are well known to those skilled in the art. For example, a single replicative cycle for poliovirus is about 6 hours in a mammalian cell in in vitro cell culture; and a single replicative cycle for HCV is about 48 hours in a mammalian cell in in vitro cell culture.

Whether a parent virus interferes with growth of a variant virus during at least one replicative cycle is readily determined using known methods. For example, growth of the parent virus and growth of the variant virus is determined in in vitro culture. The parent virus and the variant virus are introduced into a mammalian cell in in vitro culture; and the effect, if any, of growth of the parent virus on growth of the variant virus is determined.

In some embodiments, the effect of growth of the parent RNA virus on growth of the variant virus is determined by introducing both parent RNA virus and variant RNA virus into mammalian cells in in vitro culture, where the parent RNA virus is introduced into mammalian cells at a multiplicity of infection (MOI; or the average number of virus genomes per cell) of from about 1 to about 100, e.g., the parent RNA virus is introduced into mammalian cells at an MOI of from about 1 to about 5, from about 5 to about 10, from about 10 to about 20, from about 20 to about 30, from about 30 to about 40, from about 40 to about 50, from about 50 to about 70, or from about 70 to about 100; and the variant RNA virus is introduced into the mammalian cells at an MOI of from about 0.01 to about 1, e.g., the variant RNA virus is introduced into the mammalian cells at an MOI of from about 0.01 to about 0.05, from about 0.05 to about 0.07, from about 0.07 to about 0.1, from about 0.1 to about 0.2, from about 0.2 to about 0.5, or from about 0.5 to about 1.0. In some embodiments, the ratio of MOI of the parent virus to the variant virus is from about 5 to about $10^4$, e.g., from about 5 to about 10, from about 10 to about $10^2$, from about $10^2$ to about $5\times10^2$, from about $5\times10^2$ to about $10^3$, from about $10^3$ to about $5\times10^3$, or from about $5\times10^3$ to about $10^4$.

Growth of the drug-sensitive, parent RNA virus inhibits growth of the drug-resistant, variant RNA virus, e.g., the yield of drug-resistant, variant RNA virus is reduced. For example, growth of the drug-sensitive, parent RNA virus reduces the yield of drug-resistant, variant RNA virus per cell in in vitro mammalian culture by at least about 10%, at least about 20%, at least about 25%, at least about 30%, at least about 35%, at least about 40%, at least about 50%, at least about 60%, at least about 70%, at least about 80%, or at least about 90%, or more (e.g., at least about 95%, at least about 98%), during at least one replicative cycle (e.g., during one, two, three, four, five, or more replicative cycles). In some embodiments, yield of the drug-resistant, variant RNA virus is undetectable during one or more replicative cycles.

In some embodiments, step (a) is carried out in the absence of the test agent; and determining the effect of growth of the parent RNA virus on the variant virus is carried out using a plaque assay in the presence and in the absence of the test agent. In the absence of the test agent, the plaque assay provides the total number of viruses (parent+variant); and in the presence of the test agent, the plaque assay provides the number of variant virus. A control can be carried out, in which mammalian cells are culture in vitro, which mammalian cell comprise only the variant RNA virus; and the number of variant virus determined using a plaque assay in the presence and absence of the test agent. An example of such an assay is depicted schematically in FIG. 8.

Virus growth in vitro is readily measured using known assays. For example, in some embodiments, virus produced by a cell is harvested and virus stocks are determined by plaque assay. As another example, the parent virus and the variant virus could be constructed such that the parent virus includes a first reporter gene operably linked to a promoter; and the variant virus includes a second reporter gene operably linked to a promoter, where the first and second reporter genes encode products that are distinguishable from one another; and the effect of parent virus growth on variant virus growth is determined by detecting the first and second gene products. As another example, viral RNA is measured within the cell or in cell extracts or supernatants, virion production is measured by viral capsid or envelope protein in the supernatant.

Suitable reporter gene products include, but are not limited to, luciferase (e.g., firefly luciferase and derivatives thereof; *Renilla* luciferase and derivatives thereof); β-galactosidase; chloramphenicol acetyl transferase; glutathione S transferase; a green fluorescent protein (GFP), including, but not limited to, a GFP derived from *Aequoria victoria* or a derivative thereof, a number of which are commercially available; a GFP from a species such as *Renilla reniformis, Renilla mullen*, or *Ptiosarcus guernyl*, as described in, e.g., WO 99/49019 and Peelle et al. (2001) *J. Protein Chem.* 20:507-519; any of a variety of fluorescent and colored proteins from *Anthozoan* species, as described in, e.g., Matz et al. (1999) *Nature Biotechnol.* 17:969-973, U.S. Patent Publication No. 2002/01 97676, or U.S. Patent Publication No. 2005/0032085; a red fluorescent protein; a yellow fluorescent protein; a LUMIO™ tag (e.g., a peptide which is specifically bound by a fluorescein derivative having two As(III) substituents, e.g., 4',5'-bis(1,3,2-dithioarsolan-2-yl)fluorescein; see, e.g., Griffin et al. (1998) *Science* 281 :269; Griffin et al. (2000) *Methods Enzymol.* 327:565; and Adams et al. (2002) *J. Am. Chem. Soc.* 124:6063); and the like.

Growth of the drug-sensitive, parent RNA virus inhibits growth of the drug-resistant variant RNA virus, e.g., the yield of drug-resistant, variant RNA virus is reduced. However, in some embodiments, poduction of variant viral RNA in the cytoplasm is unaffected by growth of the parent RNA virus. Whether production of variant virus RNA is reduced by growth of the parent RNA virus is readily determined using known assays. For example, RNA can be harvested from cells, and the amounts of parent and variant virus determined using a reverse-transcription/polymerase chain reaction (RT-PCR) method.

Suitable mammalian cells include primary cells and immortalized cell lines. Suitable mammalian cell lines include human cell lines, non-human primate cell lines, rodent (e.g., mouse rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH3T3 cells (e.g., ATCC No. CRL-1658), Huh-7 Cells, BHK cells (e.g., ATCC No. CCL10), PC12 cells (ATCC No. CRL1721), COS Cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Parent RNA virus and variant RNA virus are introduced into the mammalian cell in vitro using any of a variety of methods, a number of which are well known in the art. For example, where the virus is an encapsidated virion, the virus can be introduced into a mammalian cell by infection. Where the virus is not encapsidated (e.g., the virus is in the form of non-encapsidated RNA or other non-encapsidated nucleic acid), the virus can be introduced into a mammalian cell by electroporation, transfection using DEAE-dextran, lipofection, and the like. DNA plasmids that encode the viral RNAs can also be used.

Virus growth in vivo is readily measured using known assays. For example, a mammal (e.g., a rodent) is infected with both parent and variant viruses, and virus growth is measured at various times post-infection. Virus may be harvested from specific tissues or organs (e.g. skin, brain, muscle, spleen, etc.) and the tissue disrupted (e.g. by sonication, freeze-thaw followed by mortar/pestle grinding, homogenization using blender or dounce, etc) and the emerging virus quantified by plaque assay or reporter gene assay as described above. Virus growth can be measured by plaque assay or by detection of viral products in the cell supernatant or by detection of intracellular viral genomes.

Parent RNA Virus

A parent RNA virus that is suitable for use in a subject method exhibits sensitivity to one or more test agents, e.g., a test agent inhibits growth of the parent RNA virus. Parent RNA viruses that are suitable for use in a subject method include wild-type RNA virus; wild-type RNA genome; any known serotype of an RNA virus; a DNA copy of a wild-type RNA genome; replication-competent variants of a wild-type RNA virus that retain sensitivity of a wild-type virus to a selected test agent and is capable of replication in a mammalian host cell; recombinant constructs comprising an RNA virus genome, or a DNA copy of an RNA virus genome; and sub-genomic replicons that retain sensitivity of a wild-type virus to a selected test agent.

Suitable parent RNA viruses include positive-strand RNA viruses and negative-strand RNA viruses. Suitable positive-strand RNA viruses include, but are not limited to, members of Picornaviridae, Flaviviridae, Togaviridae, Caliciviridae, Coronaviridae, and Retroviridae families. Positive-strand RNA viruses generally (except retroviruses) share the following features: replicate in the cytoplasm; genomic RNA serves as a message and is translated; genomic RNA is infectious; virions do not contain any enzymes; and viral proteins are translated as polyproteins.

Picornaviridae family members include, but are not limited to, members of genus Enterovirus (including poliovirus, enterovirus, coxsackievirus, echovirus); members of the genus Rhinovirus; members of the genus Hepatovirus (hepatitis A virus); encephalomyocarditis virus (EMCV); and foot-and-mouth disease virus (FMDV).

Flaviviridae family members include, but are not limited to, members of the genus flavivirus, e.g., Dengue virus, Yellow Fever Virus, St. Louis encephalitis virus, Japanese encephalitis virus, and West Nile virus; members of the genus hepacivirus, e.g., hepatitis C virus; and members of the genus pestivirus, e.g., bovine viral diarrhoea virus (BVDV).

Togaviridae family members include members of the genus alphavirus, e.g., Eastern encephalitis, western encephalitis, Sindbis, and Semliki forest viruses; and members of the genus rubivirus, e.g., rubella virus.

Retroviridae family members include members of the genus lentiviruses including, but not limited to, human immunodeficiency virus, simian immunodeficiency virus (SIV), and feline immunodeficiency virus.

Suitable negative-strand RNA viruses include, but are not limited to, Filoviridae family members (including Marburg virus, Ebola virus); Orthomyxoviridae family members (including influenza virus); Paramyxoviridae family members (including measles virus), and Rhabdoviridae family members (including rabies virus).

In some embodiments, a parent virus is a recombinant construct comprising an RNA virus genome, or a DNA copy of an RNA virus genome. The entire RNA genome (or a DNA copy thereof) may be present; however, the entire RNA genome (or a DNA copy thereof) need not be present in the recombinant construct. Suitable constructs include plasmid constructs that include a cDNA copy of an RNA virus genome, or a sub-genomic portion of an RNA virus genome. Sub-genomic replicons of HCV are known in the art and include, e.g., those described in U.S. Pat. No. 6,956,117.

Poliovirus is exemplified in the Examples, below. Nucleotide and amino acid sequences of poliovirus are known in the art. For example, the nucleotide sequence of poliovirus type 1 (Mahoney strain) is set forth in GenBank Accession No. NC_002058; and is presented as SEQ ID NO:1; and amino acid sequences of the encoded proteins are set forth in GenBank Accession No. NP_041277; and presented as SEQ ID NO:2. Amino acid sequences of individual proteins encoded by poliovirus type 1 (Mahoney) are provided in GenBank Accession Nos. NP_740469 (VP2; SEQ ID NO:3; and FIG. 9); NP_740470 (VP3; SEQ ID NO:4; and FIG. 10); NP_740471 (VP1; SEQ ID NO:5; and FIG. 11); NP_740477 (2A; SEQ ID NO:6; and FIG. 12); NP_740472 (2B; SEQ ID NO:7; and FIG. 13); NP_740473 (2C; SEQ ID NO:8; and FIG. 14); NP_740474 (3A; SEQ ID NO:9; and FIG. 15); NP_740475 (3B; SEQ ID NO:10; and FIG. 16); NP_740476 (3C; SEQ ID NO:11; and FIG. 17); NP_740478 (3D; SEQ ID NO:12; and FIG. 18); and NP_740468 (VP4; SEQ ID NO:13 and FIG. 19). Sequences of poliovirus type 3 (Fox strain) are set forth in GenBank Accession No. AY359875. Sequences of poliovirus type 3 (Sabin) are set forth in GenBank Accession Nos. X00596 and P03302.

Variant RNA Virus

A variant RNA virus is a variant of any of the above-described parent RNA virus that, unlike the parent RNA virus, is resistant to a particular agent, e.g., the variant virus grows in a mammalian cell in the presence of a selected test agent. Thus, e.g., where growth of a parent RNA virus is inhibited by a selected test agent, growth of a variant of the parent RNA virus is resistant to the test agent.

A variant RNA virus genome comprises one or more changes in nucleotide sequence relative to the nucleotide sequence of the parent RNA virus genome. The one or more changes in nucleotide sequence result in a change in the RNA and/or an encoded protein that inhibits growth of the parent virus RNA in a mammalian cell containing both parent virus RNA and variant virus RNA when the cell is cultured in the absence of a test agent. Thus, the one or more changes in nucleotide sequence result in a change that provides for a dominant-negative phenotype when parent virus and a variant virus are present together in the same mammalian cell in the absence of any test agent. In some embodiments, the one or more changes in nucleotide sequence result in a change in viral RNA or viral-encoded protein such that the variant virus, is non-viable when grown in the absence of parent virus (or any other wild-type virus or any other virus that compensates for the mutation) in a mammalian cell.

As noted above, the one or more changes in nucleotide sequence result in a change that provides for a dominant-negative phenotype when parent virus and a variant virus are present together in the same mammalian cell in the absence of any test agent. Thus, e.g., when variant RNA virus and parent virus are introduced into mammalian cells in in vitro cell culture in the absence of test agent, and at an excess of variant virus over parent virus, the variant virus reduces parent viral growth by at least about 10%, at least about 20%, at least about 25%, at least about 30%, at least about 35%, at least about 40%, at least about 50%, at least about 60%, at least about 70%, at least about 80%, or at least about 90%, or more (e.g., at least about 95%, at least about 98%), during at least one replicative cycle.

In some embodiments, the variant RNA virus comprises one or more changes in nucleotide sequence, compared to the nucleotide sequence of the parent RNA virus, where the one or more nucleotide sequence changes alter the amino acid sequence of an encoded viral oligomeric protein, such that the virus produces a variant viral oligomeric protein in the cytoplasm of a mammalian cell. Variant viral oligomeric proteins include variants having one or more amino acid sequence changes relative to the parent oligomeric protein, where amino acid sequence changes include insertions, deletions, truncations, substitutions, etc. In some embodiments, a variant viral oligomeric protein has a single amino acid substitution, compared with the parent viral oligomeric protein. The variant oligomeric protein inhibits growth of a parent virus present in the same cell. Oligomeric viral proteins that, when mutated, exhibit a dominant negative phenotype, include, but are not limited to, viral capsid proteins; membrane-associated proteins; and polymerases (e.g., RNA-dependent RNA polymerase).

In some embodiments, the variant RNA virus comprises one or more changes in nucleotide sequence, compared to the nucleotide sequence of the parent RNA virus, where the one or more nucleotide sequence changes alter the amino acid sequence of an encoded viral trans-acting protein. Variant viral trans-acting proteins include variants having one or more amino acid sequence changes relative to the parent trans-acting protein, where amino acid sequence changes include insertions, deletions, truncations, substitutions, etc. In some embodiments, a variant viral trans-acting protein has a single amino acid substitution, compared with the parent viral trans-acting protein. The variant trans-acting protein inhibits growth of a parent virus present in the same cell. Trans-acting proteins include, but are not limited to, protein primer; polymerases, proteinases that cleave polyproteins; RNA helicases; membrane associated proteins, and the like.

Identification of Dominant Negative Protein Targets

Suitable viral variants can be identified using a method as follows. In some embodiments, a target for anti-viral drug intervention is identified by a method comprising: a) introducing a mutation into a coding region of the genome of a parent RNA virus, generating a variant RNA virus comprising a variant coding region; b) co-transfecting a mammalian cell in vitro with the parent RNA virus and the variant RNA virus; and c) determining the effect, if any, of the variant RNA virus on growth of the wild-type RNA virus. Inhibition of growth of the parent RNA virus by the variant RNA virus indicates that the product of the variant coding region is a suitable target for anti-viral drug intervention.

Methods for introducing mutations into a coding region of a viral genome are well known in the art, and any known method can be used. Mutations that are introduced into the viral genome result in one or more changes in amino acid sequence of an encoded viral protein, relative to the amino acid sequence of the viral protein encoded by the parent RNA virus. Mutations include random mutations and directed (non-random) mutations.

Methods of mutating a nucleic acid are well known in the art and include well-established chemical mutation methods, radiation-induced mutagenesis, and methods of mutating a nucleic acid during synthesis. Chemical methods of mutating DNA include exposure of DNA to a chemical mutagen, e.g., ethyl methanesulfonate (EMS), methyl methanesulfonate (MMS), N-nitrosourea (ENU), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (e.g., diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Mutations can also be introduced into a nucleic acid using, e.g., trimethylpsoralen with ultraviolet light. Random or targeted insertion of a mobile DNA element, e.g., a transposable element, is another suitable method for generating mutations. Mutations can be introduced into a nucleic acid during amplification in a cell-free in vitro system, e.g., using a polymerase chain reaction (PCR) technique such as error-prone PCR. Non-random mutations can be introduced using a PCR method, where a primer is used that has one or more nucleotide differences from the template. Mutations can be introduced into a nucleic acid in vitro using DNA shuffling techniques (e.g., exon shuffling, domain swapping, and the like). Mutations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1-6, PMS 1-2, MLH 1, GTBP, ERCC-1, and the like). Methods of mutating nucleic acids are well known in the art, and any known method is suitable for use. See, e.g., Stemple (2004) *Nature* 5:1-6; Chiang et al. (1993) *PCR Methods Appl* 2(3): 210-217; Stemmer (1994) *Proc. Natl. Acad. Sci. USA* 91:10747-51; and U.S. Pat. Nos. 6,033,861, and 6,773,900.

The variant viral-encoded protein will have one or more changes in amino acid sequence, compared to the amino acid sequence of the same protein encoded by the parent RNA virus. Variants will have one or more amino acid substitutions, insertions, or deletions compared to the amino acid sequence of the same protein encoded by the parent RNA virus. In some embodiments, the variant viral-encoded protein will have a single amino acid substitution, compared to the amino acid sequence of the same protein encoded by the parent RNA virus. Variant RNA sequences will have one or more nucleotide changes relative to parent RNA virus.

Test Agents

The terms “candidate agent,” “test agent,” “agent,” “substance,” and “compound” are used interchangeably herein. Test agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible. The term “test agent” excludes WIN-51711.

Candidate agents may be small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In some embodiments, test agents include neutralizing antibodies. In some embodiments, neutralizing antibodies are specifically excluded.

Selecting for Drug-Resistant Viral Variants

As noted above, a subject method for identifying a candidate anti-viral agent involves culturing a mammalian cell in vitro, where the mammalian cell comprises a drug-sensitive parent RNA virus (e.g., a parent RNA virus that exhibits growth inhibition in the presence of a test agent) and a drug-resistant variant RNA virus (e.g., a variant virus, where growth of the variant virus is resistant to the test agent). Selection of a variant RNA virus that is resistant to a test agent can be carried out using standard methods. For example, mammalian cells comprising a parent RNA virus are cultured in vitro in the presence of a test agent that inhibits growth of the parent RNA virus. Variants are selected that are not growth-inhibited, and therefore are resistant to the test agent.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Identification of Dominant Targets

Methods

Design and Characterization of Mutant Genomes Used for Dominant Inhibitor Screen.

To amass a collection of nonviable mutant poliovirus genomes, previously characterized lethal mutations, or mutations that were designed to destabilize the structure of the encoded viral protein product, were introduced using two strategies. The first strategy was to disrupt the hydrophobic core of the encoded protein by reducing the size of an amino acid side chain predicted to be inaccessible to solvent or by changing it to Pro. A second strategy was to disrupt predicted α-helices by altering Leu and Ser residues predicted to reside in α-helices to Pro. A computer algorithm, PredictProtein[33], was used to predict the likely solvent accessibility and α-helicity of each amino acid position within the poliovirus type 1 (Mahoney) polyprotein in its native, folded state. Single amino acids presumed to be within the hydrophobic protein core by virtue of displaying a PredictProtein score greater than five were altered by introducing a single U-to-C transition mutation into the viral genomes, using PCR-mediated site-directed mutagenesis[34]. The PredictProtein method was used instead of known three-dimensional structures to simulate the knowledge base of other, less well-characterized, positive-strand RNA viruses.

The viability of each mutant genome was tested by transfecting 60 mm plates of subconfluent S3 HeLa monolayers with 1 µg of in vitro transcribed mutant RNA using DEAE-dextran (see below). Viral stocks were harvested after a single replicative cycle (10 hrs at 32.5° C.) by pelleting the cells at 200×g, washing and lysing by freeze-thaw in 1 ml of PBS+ (phosphate buffered saline with 0.1% $CaCl_2$ and $MgCl_2$), and lysing the cells by freeze-thaw treatment. Stocks were then titered as previously described[35]. Mutant genomes that produced no detectable plaques in this assay were defined as nonviable; 1 µg of wild-type RNA typically yielded between $4 \times 10^5$-$1 \times 10^6$ PFU under these conditions. The results of the engineered and previously characterized mutations are described in Tables 1 and 4. Reversion of mutant genomes to produce wild-type virus was not detected using DEAE-dextran transfections.

RNA Transcription and Co-Transfections

Plasmids containing the poliovirus 1 genome (pGEM-PV1) under the control of a T7 promoter were linearized by Eco R1 restriction digestion (New England Biolabs, Beverly, Mass.), purified by agarose gel electrophoresis, and used as a template for transcription using the Ribomax (Promega, Madison, Wis.) T7 transcription kit according to the manufacturer's standard protocol. A control RNA, R2-PvuII (see below), was made from pGEM-PV1 cDNA that lacks capsid encoding nucleotides 1175 to 2956 and linearized with PvuII, which cleaves within the coding region of 3D polymerase. All transcription reactions were extracted twice with acid phenol-chloroform-(5:1, pH 4.5, Ambion) to remove protein and template DNA, and precipitated with a half volume of 7.5 M ammonium acetate and 2.5 volumes ethanol. Precipitated pellets of RNA were then resuspended in water and applied to a P30 size exclusion column (Biorad, Hercules, Calif.) to remove unincorporated nucleotides and the eluate collected according to the manufacturer's protocol. The integrity of transcribed RNA was verified by denaturing formaldehyde agarose gel electrophoresis and the concentration determined by measuring absorbance at 260 nm. The preparations were reprecipitated, aliquoted and stored at −80° C. Transcription reactions were also performed in the presence of $\alpha^{32}$P-UTP to verify that RNA amounts measured by O.D. at 260 nm represented RNA transcripts and not unincorporated nucleotides.

The effect of each mutant genome on the growth of wild-type virus was tested by co-transfecting 60 mm plates of subconfluent S3 HeLa monolayers with 1 µg of in vitro transcribed mutant RNA and 100 ng of wild-type poliovirus RNA using DEAE-dextran (average molecular weight=500,000; Sigma, St. Louis, Mo.) as described previously[8]. After 10 hours incubation of each transfection at 32.5° C., cells were harvested, virus stocks produced, and plaque assays performed as described[35].

In Vitro Translation of Poliovirus RNAs and α-VP1 Immunoprecipitation of Translation Reactions Poliovirus RNAs were transcribed as for transfections. HeLa S10 extracts were prepared as previously described[36], and a 25 µl reaction was programmed with 5 µg of RNA, 50% HeLa extract, 1 µl [35]S-Met Express label (NEN), 0.5 µl RNasin (Promega), and 0.5 µl 1 mM of each amino acid except methionine. Each reaction was incubated for 2 hours at 30° C., and then stopped by addition of 2×-lysis buffer (2% Triton X-100 prepared in TBS: 10 mM Tris-Cl pH 8.0, 140 mM NaCl, and 0.025% $NaN_3$). Each reaction was then centrifuged at 10,000×g for 30 minutes at 4° C. To clear the supernatant, $1/20^{th}$ volume of a 50% slurry of protein-G sepharose beads (Gibco-BRL, Grand Island, N.Y.) was added to the supernatant, incubated at room temperature for 2 hrs, and pelleted by 1 min. centrifugation at 200×g. The supernatant was transferred to a new tube precoated with lysis buffer that contained 200 µl of dilution buffer (0.1% Triton X-100 prepared in TBS). Monoclonal mouse α-VP1 antibody (3 µg; Chemicon, Temecula, Calif.) was added to each reaction and incubated 1.5 hours at 4° C. The beads were pelleted at 200×g and washed twice with dilution buffer, once with TBS, and once with 50 mM Tris-Cl (pH 6.8). Proteins in the samples were then separated on a 10% polyacrylamide gel by SDS-PAGE analysis.

Super-Infections

Temperature-sensitive viruses were either previously described[24] or generated during the screening of nonviable poliovirus type 1 (Mahoney) mutants (Table 3). HeLa cell monolayers were infected at an MOI=100 PFU/cell with each temperature-sensitive virus at a semi-permissive temperature of 37° C. in PBS+. After virus adsorption (30 minutes), serum supplemented DMEM was added with 2 mM guanidine hydrochloride to block viral RNA synthesis. At two hours post-infection, the media was removed and cells were super-infected with wild-type virus at an MOI of 0.5 PFU/cell. Incubation at 37° C. was continued for 4 hours in the absence of guanidine, whereupon cells were harvested and virus stocks were made as described above. Virus titers were determined at 39° C.

Co-Infections of WIN-Sensitive and WIN-Resistant Viruses

WIN-resistant Sabin 3 virus was engineered by introducing a mutation, VP1-I192F, into a cDNA encoding the attenuated Sabin type 3 poliovirus. Infections and co-infections of HeLa cell monolayers at the indicated MOI's for 30 minutes at 37° C. Serum-supplemented DMEM (10%) with or without 2 µg/ml final concentration WIN-51711 was added to the cells, and incubation continued at 37° C. for 6 hours. Cells were then harvested and virus stocks titered by plaque assay in the absence and presence of 2 µg/ml WIN-51711 in the agar overlay.

RT-PCR of WIN-R and Wild-Type RNA

Co-infections and single infections of wild-type and WIN-resistant viruses were performed as described above in the absence of WIN-51711. At 5 hours post-infection, cells were harvested and processed by the addition of 1 ml Trizol (Invitrogen, Carlsbad, Calif.) to each plate and incubation for 5 min. at room temperature. The solution was extracted with 0.2 ml chloroform and the supernatants were collected. At this time, "mix" samples were created by combining equal volumes of supernatants derived from single infections (see FIGS. 6c,d) Nucleic acids were collected by the addition of isopropanol (70%), pelleting by centrifugation, washing with 70% ethanol, repelleting, and resuspension in 50 µl 10 mM HEPES-KOH (pH 7.5).

Each reverse transcriptase reaction contained 5 µl RNA sample in a final volume of 10 µl using AMV-RT High Concentration (Promega, Madison, Wis.) as recommended by the manufacturer. PCR reactions (50 µl total volume) were composed of 5 µl of a reverse transcriptase reaction and performed as previously described[37]. Reactions were cycled 35 times (94° C., 1 minute; 54° C., 1 minute; 72° C. 1 minute). Primers used amplified a region from nucleotide 2967 to 3241 of the type 3 genome. Two TfiI restriction sites (at nucleotides 3048 and 3149) exist within the wild-type PCR product, but the 3048 site is disrupted by the VP1 I192F WIN-R mutation. PCR reactions were brought to 200 µl volumes and digested with 25 units TfiI for two hours at 65° C. Reactions were then ethanol precipitated and analyzed by PAGE on a 5% polyacrylamide, 8M urea gel.

Results

Design and Characterization of Nonviable Poliovirus Mutations

To search for dominant alleles in a comprehensive, genome-wide manner, a battery of lethally mutated genomes spanning the poliovirus coding region was constructed (Table 1). The construction of each mutant genome was guided either by a previously described mutation or by a strategy to disrupt the structure of the encoded protein. By targeting predicted hydrophobic cores or α-helices (see Methods), 24 individual U-to-C mutations were introduced into an infectious poliovirus cDNA and the viability of each mutant viral genome was tested. The results of these transfections and the rationale for each mutation are shown in Table 1.

TABLE 1

Mutant poliovirus genomes constructed for use in the dominance screen.

| Mutant | Codon Change | Rationale | Viability (PFU/ml) |
|---|---|---|---|
| Previously characterized mutant poliovirus genomes | | | |
| VP2-S1P | UCG→CCG | Maturation cleavage (Ansardi and Morrow 1995) | <5 |
| VP2-S243P | UCC→CCC | Reynolds et al. 1991 | <5 |
| 2A-C109R | UGU→CGU | Catalytic proteinase cysteine (Yu and Lloyd 1991) | <5 |
| 3B-Y3H | UAC→CAC | Uridylylation site (Rothberg et al. 1978; Ambros and Baltimore 1978) | <5 |
| 3C-C147R | UGU→CGU | Catalytic proteinase cysteine (Hammerle et al. 1991) | <5 |
| 3D-F30S | UUC→UCC | Fingers-thumb interaction (Hobson et al. 2001; Hansen et al. 1997) | <5 |
| 3D-S291P | UCA→CCA | Burns et al. 1989 | <5 |
| CRE-C4465U/U4483C* | None | Goodfellow et al. 2000 | <5 |
| CRE-G4462A/U4483C* | None | Goodfellow et al. 2000 | <5 |
| Designed mutant poliovirus genomes | | | |
| VP2-F260S | UUC→UCC | Hydrophobic | <5 |
| VP3-F118S | UUU→UCU | Hydrophobic | <5 |
| VP3-L211S | CUU→CCU | Hydrophobic | <5 |
| VP1-L118P | UUA→UCA | Hydrophobic & Helix | <5 |
| 2A-S74P | UCC→CCC | Helix | t.s. |
| 2A-L98P | CUC→CCC | Hydrophobic | <5 |
| 2A-F133S | UUU→UCU | Hydrophobic | <5 |
| 2B-F13S | UUU→UCU | Hydrophobic & Helix | <5 |
| 2B-F17S | UUU→UCU | Hydrophobic & Helix | <5 |

TABLE 1-continued

Mutant poliovirus genomes constructed for use in the dominance screen.

| Mutant | Codon Change | Rationale | Viability (PFU/ml) |
|---|---|---|---|
| 2C-F28S | UUC→UCC | Hydrophobic & Helix | t.s. |
| 2C-L93P | CUU→CCU | Hydrophobic | <5 |
| 2C-F242S | UUU→UCU | Hydrophobic | <5 |
| 2C-F328S | UUU→UCU | Hydrophobic & Helix | <5 |
| 3A-L8S | UUG→UCG | Hydrophobic | <5 |
| 3A-L24S | UUG→UCG | Hydrophobic & Helix | <5 |
| 3A-F83S | UUU→UCU | Hydrophobic | <5 |
| 3C-L70P | CUU→CCU | Hydrophobic | <5 |
| 3C-L102S | UUG→UCG | Hydrophobic | <5 |
| 3D-F34L | UUU→CUU | Hydrophobic | t.s. |
| 3D-L107P | CUA→CCA | Hydrophobic | <5 |
| 3D-F191S | UUU→UCU | Hydrophobic & Helix | <5 |
| 3D-F246S | UUC→UCC | Hydrophobic & Helix | <5 |
| 3D-F296S | UUU→UCU | Hydrophobic & Helix | <5 |
| 3D-Y326H | UAU→CAU | Hydrophobic | <5 |

*Mutants in the CRE (cis-acting replication element) are double mutants because viruses containing either single mutation were viable. CRE mutations are non-coding mutations in the 2C coding region.

For 21 of the 24 designed mutations, no virus was detected upon a single cycle of growth after RNA transfection, indicating an absence of reversion to wild-type virus under these transfection conditions. The three remaining mutations gave rise to viable viruses with temperature-sensitive phenotypes that were characterized further (Table 3). For both previously published and designed mutations, only mutant genomes that displayed a 100,000-fold or greater reduction in plaque formation after RNA transfection were determined to be nonviable and used in the screen for dominant negative poliovirus alleles, which identified four classes of strongly dominant alleles.

Dominant-Negative Alleles in Capsid Coding Regions

To test the ability of nonviable mutant genomes to affect wild-type viral growth, nonviable and wild-type viral RNAs were co-transfected into HeLa cells, the intracellular virus was harvested after a single replicative cycle, and the resulting wild-type virus stocks were titered. To both mimic a scenario in which a drug-resistant genome emerges from a drug-sensitive population, and to optimize co-transfection conditions, a ten-fold excess of the nonviable genome was chosen. Total yeast tRNA was substituted for mutant RNA in the positive wild-type control. Under these conditions, a transfection of approximately $2 \times 10^6$ cells with 100 ng wild-type RNA typically yielded a virus stock of 50,000-200,000 PFU (plaque-forming units)/ml.

The effect of a known inhibitor of poliovirus RNA replication, an RNA transcript (R2-PvuII) made in vitro from a poliovirus cDNA template cleaved with Pvu II[7], was tested to ensure that the transfection protocol used led to co-transfection of the wild-type and potentially inhibitory genomes. When co-transfected with wild-type viral RNA, a ten-fold excess of R2-PvuII RNA inhibited wild-type growth (FIG. 1b), as reported previously[8]. Although the mechanism by which R2-PvuII RNA inhibits the growth of wild-type RNA is not known, the greater than 20-fold inhibition of wild-type growth observed argues that at least 95% of the cells that contained wild-type viral RNA also contained the co-transfected inhibitor RNA.

Co-transfection of several of the lethally mutated RNAs, for example fs-2956 and 3A-L24S, either had little effect or caused a slight increase in wild-type yield (FIG. 1b). Although 3A-L24S genomes contained a lethal point mutation in one coding region, it is likely that other functional trans-acting proteins produced from these mutant genomes provide helper functions for the wild-type genomes. The frame-shift control, fs-2956, occurs in the center of the VP1 coding region, and produces a truncated wild-type capsid region with termination of translation at a stop codon at nucleotide 3129. This construct appears to have also provided a helper function by the production of capsid proteins.

In contrast, all four genomes that contained lethal mutations within the capsid coding region, VP2-S1P, VP2-S243P, VP3 L211S, and VP1-L118P, reduced wild-type viral growth approximately 10- to 20-fold (FIGS. 1a,c), which was the same extent of inhibition observed for the R2-PvuII co-transfection control. On average, capsid mutant genomes inhibited wild-type growth to 7% of wild-type growth alone.

FIGS. 1a-d. Dominant inhibitor screen for capsid-coding genome regions. (a) Schematic of mutant genomes tested as dominant inhibitors of wild-type virus growth. (b) Validation of dominant inhibitor screen for R2-PvuII, a known RNA inhibitor of poliovirus growth, and two mutant alleles, a frameshift mutation at nucleotide 2956 (fs-2956) and 3A-L24S, that each provide apparent helper function. The average of each set of replicate experiments (with standard error) is shown below each set of replicates normalized to the average of the wild-type poliovirus RNA with carrier tRNA control. (c) Mutant capsid alleles mapped to the crystal structure of capsid proteins (VP4 in cyan, VP1 in yellow, VP2 in magenta, VP3 in salmon)[48]. (d) The effect of co-transfecting the indicated RNAs with wild-type RNA on yield of wild-type poliovirus is shown as in b.

Allele-Specific Inhibition by Mutations in the 3D Polymerase Coding Region

Given the known ability of the poliovirus RNA-dependent RNA polymerase to oligomerize[10], the dominance of five different non-viable alleles that contained mutations in the polymerase coding region was tested (FIGS. 2a,b). One allele, S291P, diminished wild-type viral growth to 1% of the control (FIG. 2c), and thus exerted a larger dominant effect than the R2-PvuII negative control. Two other alleles, F30S and F191S, diminished wild-type growth to 29% and 13%, respectively, and thus were co-dominant. Other alleles showed variable intermediate or helper effects and were deemed recessive. Mapped onto the fully resolved 3D polymerase structure[11], the majority of mutated residues cluster in the hydrophobic core of the fingers domain, while 3D-F30S is located at the interface between the "finger" and "thumb" domains (FIG. 2b). While verifying that the screen adequately identifies residues involved in hydrophobic interactions, the variability in observed dominance of mutant 3D polymerase alleles may reflect varying degrees of protein stability or the oligomerization potential of 3D polymerase or its precursors. Alternatively, the allele-specificity of these alleles may also reflect their mixed effects on either 3D polymerase or its precursor, 3CD protease.

FIGS. 2a-c. Effect of mutations in 3D polymerase on the yield of wild-type virus during co-transfection. (a) Schematic diagram of poliovirus genomes indicate locations of coding regions for mutant 3D polymerase alleles. (b) Mutant alleles mapped to the three-dimensional structure of 3D polymerase[11]. (c) Parallel co-transfection experiments with wild-type RNA and viral genomes containing several different mutations in the coding region for 3D polymerase are shown as in FIGS. 1a-d.

Dominant Mutations of the Protein Primer 3B and Cis-Acting Replication Element (CRE)

A surprising result came from the trans-dominant effects of mutations in the CRE, the nominally cis-acting RNA sequence that templates VPg uridylylation in vitro[14], and 3B (the VPg coding region), shown in FIG. 3a. Two non-coding double mutations in the CRE, G19A/U40C and C22U/U40C, as well as a mutation of the genome-linked structural protein, 3B-Y3H (FIG. 3b), strongly inhibited growth of co-infecting wild-type virus. The degree of inhibition was similar to, or greater than, that exerted by R2-PvuII, the co-transfection control, or any of the capsid alleles.

A "classic" dominant negative allele is one in which the function of a protein or sequence element is disrupted while an associative property, such as a protein-protein or protein RNA interaction, is retained[17]. For the dominant negative alleles of the CRE, the stem-loop structure is predicted to be maintained (FIG. 3a)[16]. The introduction of eight non-coding mutations into the CRE, however, is predicted to completely disrupt stem-loop structure and presumably any structure-specific associations[18]. This predicted loss-of-function CRE allele ("l.o.f. CRE") did not inhibit wild-type growth (FIG. 3c). Therefore, dominant inhibition by mutant CRE-containing genomes is allele-specific, presumably requiring an intact RNA stem-loop structure to form an inhibitory complex. Presumably such a complex would involve 3CD, a precursor known to bind RNA sequences in the 5' UTR as well as the CRE.[15,16]

FIGS. 3a-c. Dominant inhibitor screen in the CRE and 3B-coding regions. (a) A schematic diagram of the predicted secondary structure of the wild-type CRE, which resides in the coding region of 2C, with indicated G19A, C22U, and U40C mutations used in the dominance screen. CRE mutants G19A/U40C and C22U/U40C correspond to genomic nucleotide positions 4462/4483 and 4465/4483, respectively, and are previously published non-coding mutations[47]. 3B encodes the protein primer, VPg, to which uridyl residues are attached at Tyr-3. Asterisks (*) denote multiple non-coding nucleotides mutated to form the "l.o.f.", or putative "loss-of-function" CRE used in c[18]. (b) Co-transfection experiments were performed mixing wild-type and mutant genomes that contain the indicated mutant alleles. (c) Specificity of mutant CRE alleles. Co-transfections of wild-type and mutant genomes that contain the specified CRE alleles were performed as in FIGS. 1a-d. Mutations that specify the "l.o.f." mutant genome is illustrated in a.

Allele-Specific Dominance in 2A Proteinase Coding Region

Figure 4A:
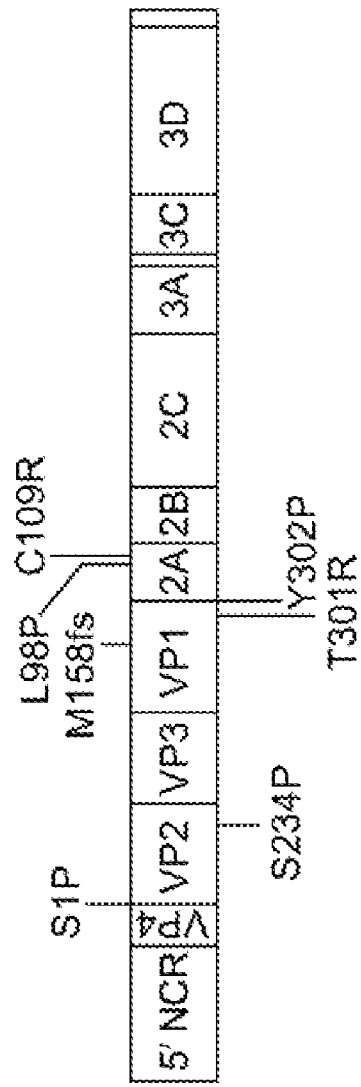

Two different mutations tested in the 2A proteinase coding region (FIGS. 4a,b) showed pronounced dominance (2A-L98P and 2A-C109R) when compared to fs-2956 (FIG. 4c). The dominant phenotype correlated with protease deficiency: FIG. 4d shows the accumulation of uncleaved VP1-2A precursor for the 2A-L98P and 2A-C109R mutations, whereas wild-type and genomes containing mutations in the capsid coding region did not[19,20]. Further experiments using only the VP1-2A region expressed in vitro recapitulated this protease-deficient phenotype.

Figure 5B:
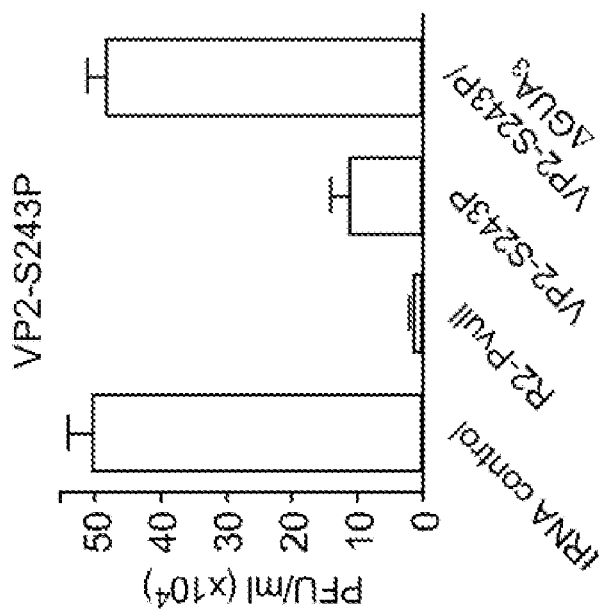
FIGS. 5A-F depict RNA replication or translation requirements for dominance of mutant poliovirus alleles.
Figure 5A:
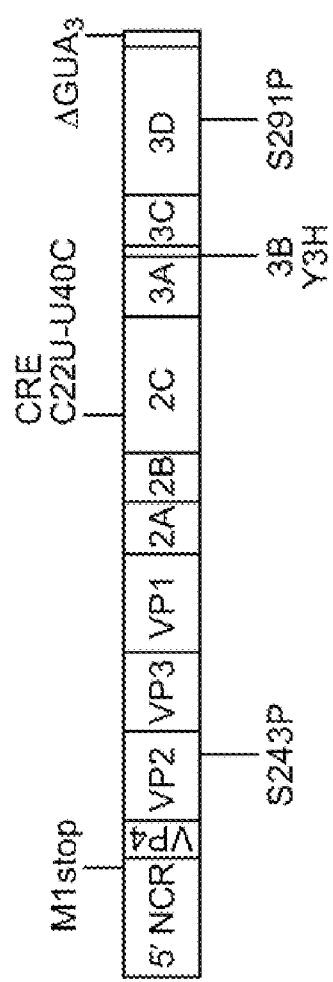
Figure 5D:
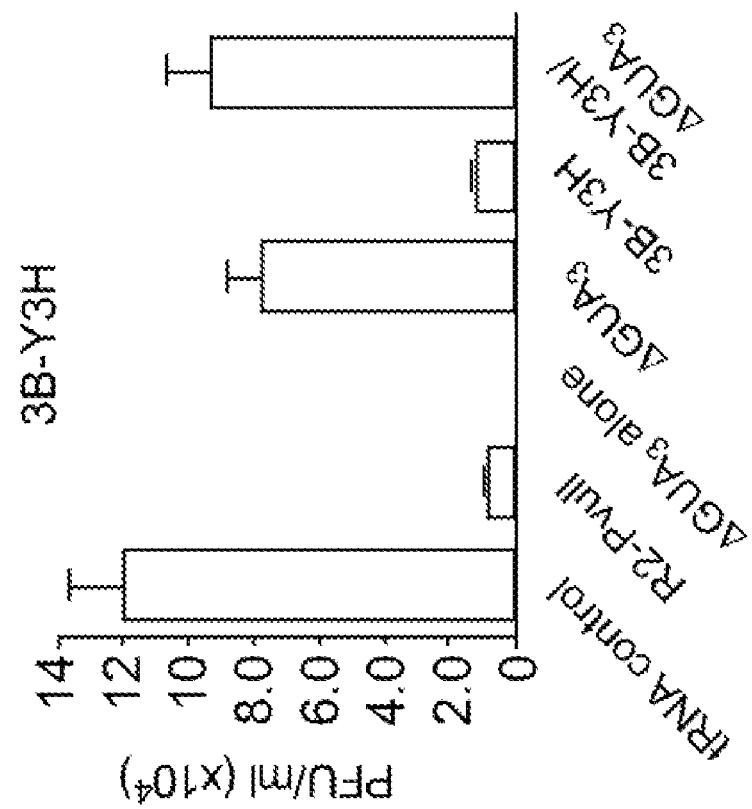
Figure 5C:
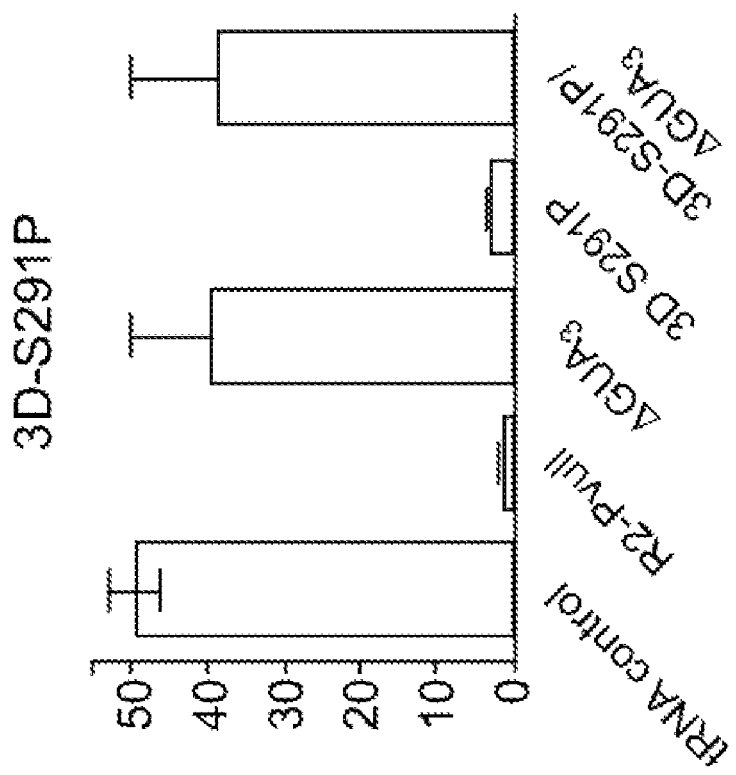

The dominance of protease-deficient 2A alleles was surprising at first, because 2A proteinase is known to be a monomeric enzyme with several viral and cellular substrates. However, its activity at the VP1-2A cleavage site is thought to be obligately intramolecular, because cleavage is unaffected by α-2A antibodies, and occurs more rapidly and with more specificity than intermolecular 2A proteinase cleavage[21,22]. A 2A protein that lacked enzymatic activity could therefore yield an uncleaved VP1-2A fusion molecule that functioned as a dominant negative inhibitor of wild-type growth, like a mutant capsid protein. To test this hypothesis explicitly, the VP1-2A cleavage site was mutagenized to allow accumulation of the uncleaved VP1-2A product from mutant genomes, and studied its effect on the growth of co-infecting wild-type virus. Two introduced mutations reported to abrogate 2A-mediated cleavage of the VP1-2A cleavage site, VP1-Y302P and VP1-T301R[22], were also dominant (FIG. 4*e*). Therefore, uncleaved VP1-2A is toxic to co-infecting wild-type virus, and its accumulation in cells infected with 2A proteinase-deficient mutant viruses is a likely mechanism for its genetic dominance.

FIGS. 4A-E. Dominant inhibitor screen for 2A proteinase and VP1-2A cleavage site mutant alleles. (a) Schematic diagram of poliovirus genomes indicate relative locations of coding regions for 2A and VP1, and the 2A proteinase and VP1-2A cleavage site mutants used in the dominant inhibitor screen. (b) 2A proteinase amino acid residues targeted to generate nonviable mutations used in the dominance inhibitor screen and superinfection assay are mapped onto the crystal structure of 2A proteinase from human rhinovirus 2, a closely related homolog of poliovirus 2A proteinase[49]. (c) Co-transfections were performed as in FIG. 1 and the resulting wild-type virus yields of replicate experiments are shown. Normalization of these values as a percentage of the wild-type RNA with tRNA carrier control is shown at bottom with standard error. (d) HeLa cytoplasmic lysates were programmed with the indicated poliovirus RNAs and labeled using $^{35}$S-methionine (Methods), immunoprecipitated with a monoclonal anti-VP1 antibody, and separated on a 10% SDS-PAGE gel. VP1 and VP1-2A mobilities are marked. The asterisk (*) denotes a higher molecular weight species abundant in 2A-L98P and 2A-C109R reactions. (e) Testing for dominance of genomes with mutated VP1-2A sites was performed as in FIGS. 1*a-d*.

Translation and RNA Replication Requirements for Dominance

Genomes that contain mutant capsid alleles are usually known to be competent for RNA replication; therefore, the observed dominance of genomes with capsid mutations may be augmented by the replication of the mutant genomes, resulting in the production of high concentrations of mutant capsid proteins. To determine whether or not mutant capsid alleles require RNA replication to exert their dominant effect, a second mutation, $\Delta GUA_3$, was introduced into one of the dominant mutant genomes. The deletion of nucleotides 7418-7422 in the 3'-non-coding region (FIG. 5*a*) is known to severely diminish negative-strand RNA synthesis[9]. As shown in FIG. 5*b*, the doubly mutant genome VP2-S243P/$\Delta GUA_3$ did not inhibit wild-type virus growth. Therefore, the dominance of the VP2-S243P allele, and probably the other capsid alleles as well, requires replication of the mutant RNA genome, presumably leading to increased accumulation of the VP2-S243P mutant capsid proteins.

As with capsid alleles, 3D polymerase functions can be rescued in trans by polymerase molecules encoded by the co-transfected wild-type genomes, thus enabling genomes harboring mutant 3D polymerase alleles to replicate[8,12,13]. Whether the dominance of the 3D-S291P allele required RNA replication of its genome by introducing the $\Delta GUA_3$ deletion was tested. As shown in FIG. 5*c*, the 3D-S291P allele was no longer dominant when RNA replication of its genome was inhibited. Like the inhibitory effects of mutant capsid proteins, the high concentration of defective polymerases provided by a replicating genome is needed to inhibit the growth of co-infecting wild-type virus.

To test whether the observed dominance of the 3B mutation required RNA replication of the nonviable genome to exert dominance, the $\Delta GUA_3$ mutation was introduced. Like dominant capsid and polymerase alleles, the 3B-Y3H allele required replication of its RNA genome to exhibit dominant negative effects on wild-type growth (FIG. 5d).

Figure 5F:
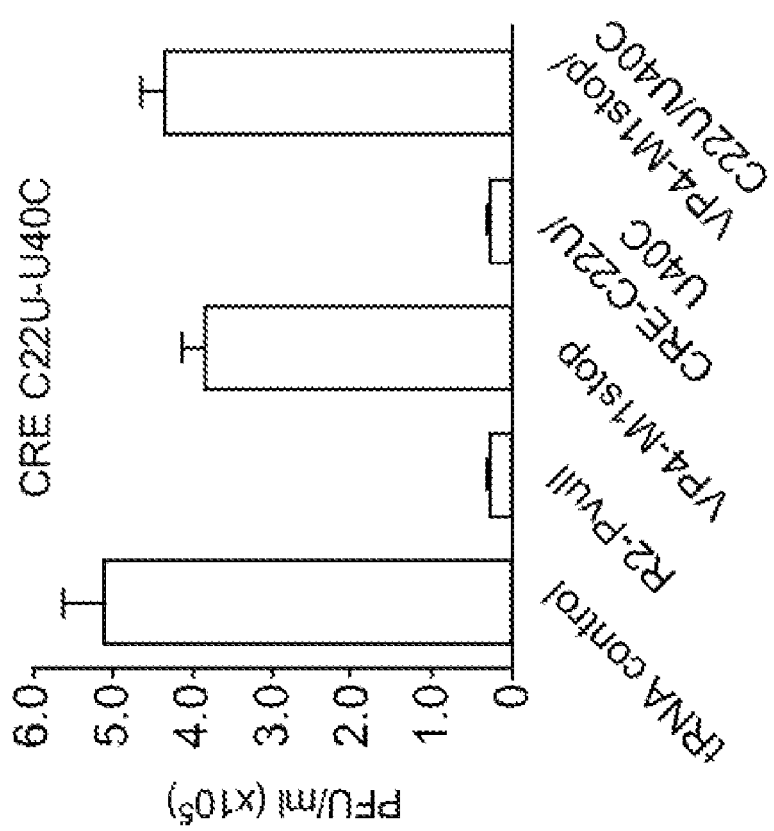
Figure 5E:
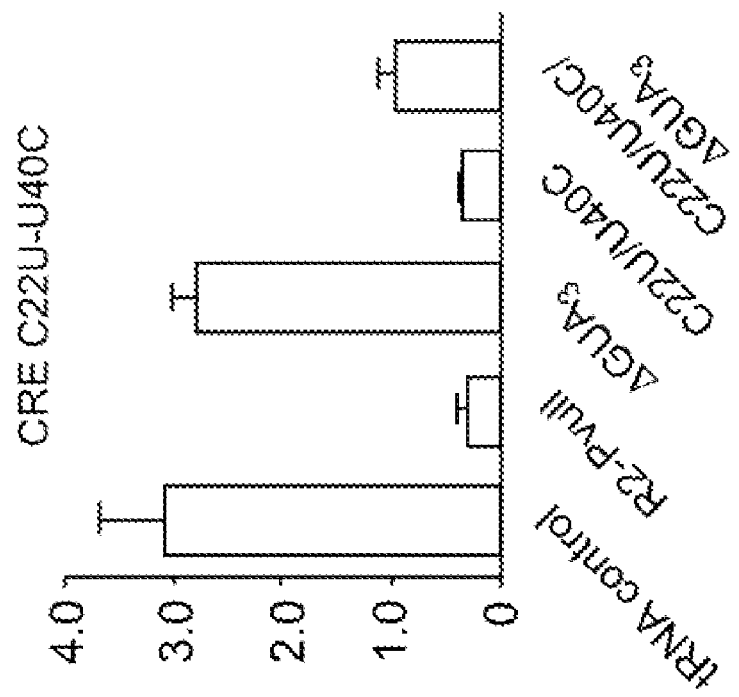

However, when the same experiment was performed with dominant negative CRE allele C22U/U40C, the triple mutant C22U/U40C/$\Delta GUA_3$ was still inhibitory, arguing that the mutant CRE structure was toxic at lower concentrations than the defective capsid, polymerase, or VPg proteins (FIG. 5e). That such a dominant negative effect could occur without RNA replication is not without precedent since our dominant negative control for co-transfection, R2-PvuII, lacks a 3'-non-coding region and also presumably lacks the ability to replicate. To determine whether the CRE RNA alone was the inhibitory moiety, it was undertaken to determine whether a non-translatable CRE-C22U/U40C genome was dominant. To this end, the initial methionine of the poliovirus polyprotein was mutated to an amber stop codon (VP4-M1stop), and introduced into a genome containing the C22U/U40C CRE allele. As shown in FIG. 5f, the dominant negative phenotype of the C22U/U40C CRE allele was eliminated when normal translation of the genome was blocked, arguing that it is not the CRE RNA alone, but some complex formed upon translation of viral proteins that inhibits the growth of other viruses in the same cell.

FIGS. 5A-F. RNA replication or translation requirements for dominance of mutant poliovirus alleles. (a) Schematic of mutant alleles mapped to the poliovirus genome assayed for dominance requirements. $\Delta GUA_3$ is a genome lacking nucleotides $G_{7418}UAAA_{7422}$; RNAs that contain this 3'-non-coding region deletion are deficient for negative strand synthesis[36]. The VP4-M1stop mutation changes the initial methionine of VP4 to a UAG stop codon. (b) Test of replication requirement for dominance of VP2-S243P genome. Co-transfections were performed in triplicate and are graphed as the average of replicate co-transfections with error bars to indicate standard error. (c) RNA replication requirements for 3D S291P. A mutant genome containing both the 3D-S291P and ΔGUA3 deletion was co-transfected with wild-type RNA and graphed as in b. The co-transfection of wild-type and a genome containing only the ΔGUA3 deletion is shown as a control. (d) RNA replication requirements for a mutant allele of the RNA replication protein primer, 3B-Y3H. Co-transfections were performed and graphed as in b, above. "$\Delta GUA_3$ alone" indicates that no wild-type RNA was co-transfected, while "$\Delta GUA_3$" indicates a co-transfection of that RNA with wild-type virus. "3B Y3H/$\Delta GUA_3$" indicates the co-transfection of a non-replicating RNA that contains both mutations with wild-type RNA. No virus was detected at the highest dilution of the $\Delta GUA_3$ virus alone, so the limit of detection is graphed. (e) RNA replication requirements for mutant CRE allele dominance. Co-transfections were performed as in b. "C22U/U40C/ΔGUA3" refers to the doubly mutant, non-replicating genome that contains the mutant CRE allele and 3'-non-coding region deletion. (f) Translation requirements for dominance of mutant CRE allele C22U/U40C. Co-transfections of the indicated genomes containing mutant alleles are shown as in b. "VP4-M1stop/C22U/U40C" is a non-translating genome that contains all indicated mutations.

Effects in Other Nonstructural Protein Coding Regions

The effect of mutations in the 2B, 2C, 3A, and 3C coding regions on co-transfected wild-type viral genomes is shown in Table 2.

TABLE 2

Dominant inhibitor screen results of mutant 2B, 2C, 3A, and 3C alleles.

| | PFU/ml ($\times 10^4$) | Percentage of control |
|---|---|---|
| tRNA control* | 23 | 100 ± 29% |
| R2-PvuII | 0.49 | 2 ± 1 |
| 2B F13S | 2.5 | 11 ± 2 |
| 2B F17S | 2.7 | 11 ± 5 |
| 2C L93P | 18 | 76 ± 15 |
| 2C F242S | 5.0 | 21 ± 13 |
| 2C F328S | 10 | 44 ± 13 |
| 3A L8S | 2.0 | 9 ± 2 |
| 3A F83S | 10 | 44 ± 7 |
| tRNA control* | 24 | 100 ± 19% |
| R2-PvuII | 2.0 | 8 ± 2 |
| 3C-L70P | 35 | 144 ± 32 |
| 3C-L102S | 54 | 226 ± 31 |
| 3C-C147R | 57 | 239 ± 26 |
| 2A-F133S | 54 | 224 ± 35 |

*Independent sets of co-transfections are shown.

Of the three membrane-associated proteins 2B, 2C, and 3A, mutations in 2B were found to be more consistently dominant, although their suppression of wild-type growth was not as pronounced as that of the R2-PvuII control. Partially dominant mutations in the 2B coding region have been reported previously[23], although the mechanism of dominance remains unknown. Unlike mutations in 2A proteinase (FIG. 4), mutations in 3C proteinase were either recessive or gave rise to viruses that provided a helper function (Table 2).

Superinfections of Temperature-Sensitive and Wild-Type Polioviruses.

To test whether the locus- and allele-specific dominance of co-transfected genomes would also be observed with viable viruses, the ability of temperature-sensitive (ts) viruses (FIG. 6*a*) to inhibit the growth of wild-type virus was monitored (Methods). First, cells were infected with ts mutant viruses in the presence of an RNA replication inhibitor, guanidine hydrochloride, to allow mutant viral proteins to accumulate to similar concentrations for each of the ts mutant viruses. At a later time point, guanidine was removed, wild-type virus was added, and a single cycle of viral growth continued at a semi-permissive temperature. The resulting virus stocks were then titered at a non-permissive temperature to quantify the yield of wild-type virus. As shown in FIG. 6*b*, two mutant viruses with mutations in the 2A proteinase (S74P) and 2C NTPase (F28S) coding regions did not hinder wild-type growth. However, a virus that contained a mutation in the capsid coding region[24] (VP2-R76Q) reduced wild-type virus growth by more than 260-fold compared to wild-type growth alone (FIG. 6*c*).

FIGS. 6A-C Superinfections of wild-type and temperature-sensitive polioviruses. HeLa cells were infected with the temperature-sensitive poliovirus indicated while blocking RNA synthesis as described in Materials and Methods. After mutant proteins were allowed to accumulate, wild-type poliovirus was added to HeLa cells as indicated, and the block to RNA synthesis released. Viral titers after a single cycle of infection are shown above for two separate experiments at the restrictive temperature. (a) Schematic of temperature-sensitive alleles used in superinfections. (b) Yield of wild-type virus following superinfection of cells that had accumulated protein from temperature-sensitive mutant viruses 2A-S74P or 2C-F28S (Table 3) as temperature sensitive viruses. (c)

Yield of wild-type virus following superinfection of cell that had accumulated proteins from temperature-sensitive mutant viruses VP2-R76Q[24], 3D-F34L (Table 3), or 3D-T367I[25].

Two viruses with different mutations in the coding region for the viral RNA-dependent RNA polymerase, 3D-F34L and 3D-T367I (Table 3)[25], were tested for their ability to hinder wild-type growth. While 3D-T367I virus was not inhibitory, 3D-F34L exhibited a four-fold inhibition of wild-type virus growth, thus showing that dominance of mutant genomes differed between coding regions and between alleles of the same coding region.

TABLE 3

Phenotypes of temperature-sensitive polioviruses generated by hydrophobic mutations.

| | | Phenotype | | |
|---|---|---|---|---|
| | PFU/µg RNA | 32.5° C. | 39° C. | PFU 39° C./ 32.5° C. |
| wild-type | 290 | large plaque | large plaque | 1.4 |
| 2A-S74P | 190 | very small plaque | none detected | <0.07 |
| 2C-F28S | 140 | small plaque | small plaque | 0.05 |
| 3D-F34L | 990 | small plaque | very small plaque | 0.4 |

Summary of Dominant Negative Alleles

Figure 4E:
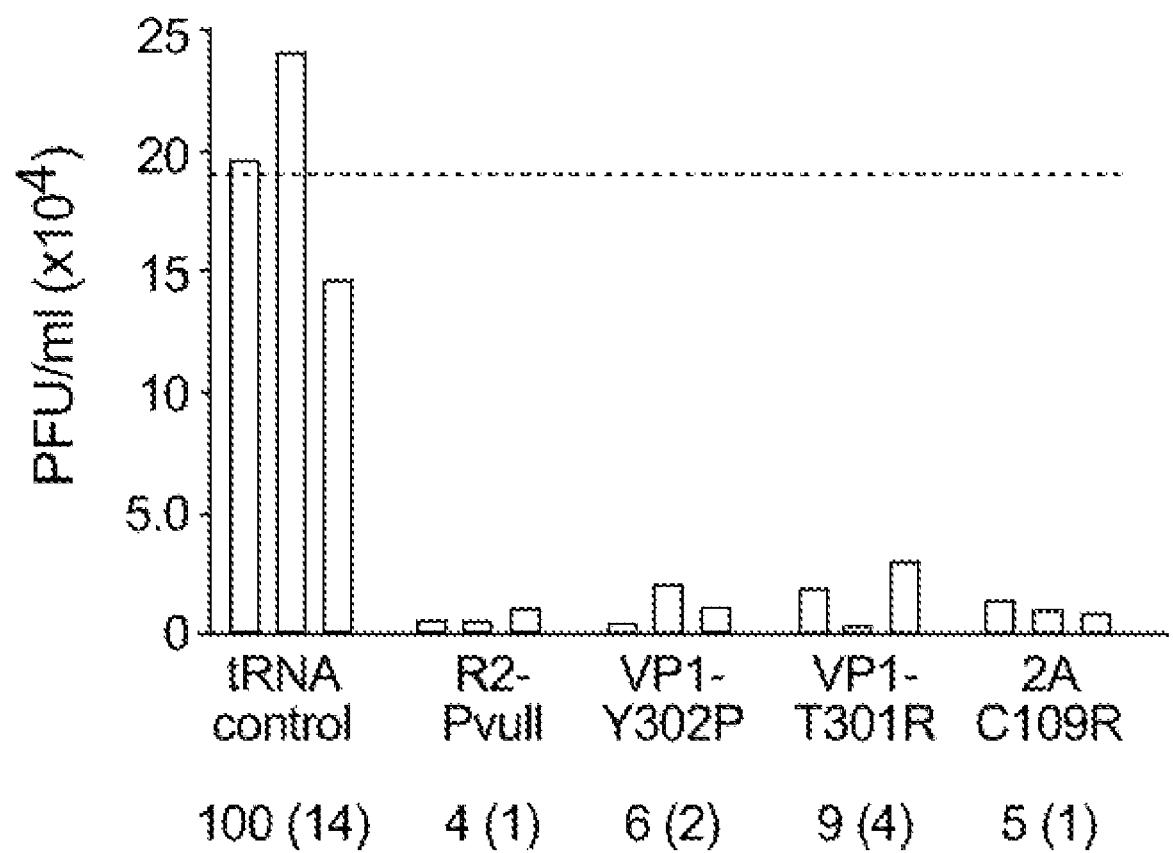

A genomic screen with poliovirus, a positive-strand RNA virus, was conducted to identify viral proteins that, when made nonfunctional by mutation, would dominantly interfere with the growth of co-transfected wild-type viral RNA genomes. These proteins should constitute ideal drug targets if the defects of the dominant alleles can be phenocopied by the antiviral compounds. Twenty-seven different genomes, each of which contained a single lethal mutation, were tested. Four classes of strongly dominant mutations were observed (Table 4). First, capsid mutations were dominant, presumably because nonfunctional mutant capsids co-assemble with wild-type capsids and render them nonfunctional. A second class of dominant genomes contained mutations in the poliovirus polymerase coding region; however, only two out of seven mutations in the polymerase coding region were strongly dominant. Poliovirus polymerase is known to oligomerize[10]; therefore, the mechanism of dominance is likely to be similar to that of the capsid alleles. A third class of strongly dominant mutations in poliovirus was found in an RNA structure, termed the CRE, that is required for generation of the protein primer for polioviral RNA synthesis. Finally, mutants that rendered the 2A proteinase of poliovirus inactive (L98P and C109R, FIG. 4) were dominant and profoundly inhibitory. The cleavage between VP1 and 2A coding regions within the viral polyprotein is made by 2A proteinase and reported to be intramolecular[21], and would therefore be refractive to scission in a mutant proteinase even in the presence of mature, wild-type 2A proteinase encoded by coinfecting genomes. Uncleaved VP1-2A protein encoded by the mutant genomes may inhibit co-infecting genomes in the same way that mutant capsid protein does, by co-assembling with wild-type capsids and poisoning their function. To test this hypothesis, the effects of directly mutating the VP1-2A cleavage site were determined. These mutants were also dominant.

TABLE 4

Summary of dominant negative alleles of poliovirus.

| | Potential Mechanism |
|---|---|
| Recessive or cis-Dominant Alleles[a] | |
| 2A-F133S, VP4-M1stop | Translation defect |
| 2C NTPase (L93P) | Potentially misfolded protein |
| 3A (L24S) | Potentially misfolded protein |
| 3C proteinase (L70P, L102S, C147R) | Potentially misfolded protein |
| 3D polymerase (L107P, F246S, F296S) | Potentially misfolded protein |
| CRE "l.o.f." (C13U/A16C/G19A/C22U/ G25A/A26U/G27C/A31G) | Unfolded RNA |
| Co-dominant Alleles[b] | |
| 2B (F13S, F17S) | |
| 3D polymerase (F30S, F191S) | |
| 3A (L8S, F83S) | |
| Dominant Alleles[c] | |
| Capsid (VP2-S1P, VP2-S243P, VP3-L211S, VP1-L118P) | Chimeric encapsidation of wild-type genomes |
| 2A proteinase (L98P, C109R) | Defect in intramolecular cleavage yields toxic precursor |
| 3D polymerase (S291P) | Chimeric oligomers |
| CRE (G19A/U40C, C22U/U40C) or VPg (3B-Y3H) | Arrested RNA replication or priming complex |

[a]Greater than 80% of wild-type control.
[b]Less than or equal to 80% of wild-type control and greater than R2-PvuII control.
[c]Less than or equal to R2-PvuII control.

Example 2

Drug-Sensitive Virus Inhibits Growth of Drug-Resistant Virus, where the Drug Target is a Dominant Target Methods The methods are described in Example 1.

Results

The Presence of a Drug-Sensitive Virus Inhibits a Drug-Resistant Virus

Figure 7A:
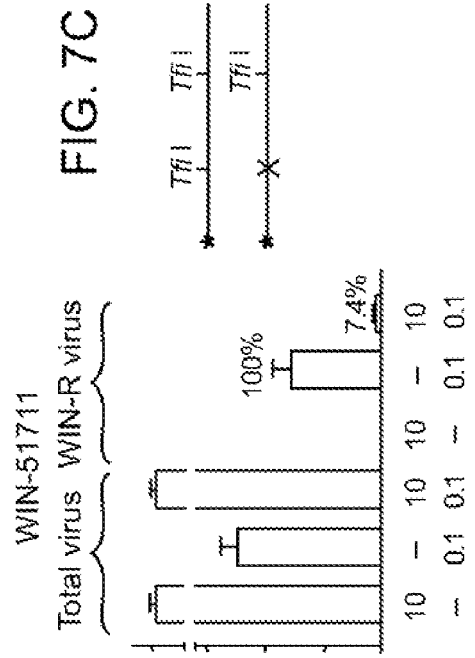
Figure 7B:
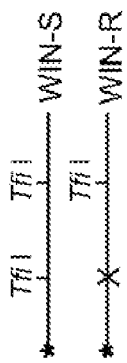

The trans-acting, highly oligomeric nature of capsid proteins and the observed dominance of mutant capsid alleles suggested that a drug-resistant virus may inhibit a drug-sensitive virus if a particular drug targets a capsid protein. Disoxaril (WIN-51711) binds to the "canyon" residues of poliovirus virions, and through stabilization of the virion structure, prevents the uncoating of the viral genome after viral cell entry[26,27]. A mutation known to confer WIN resistance, VP1-I192F, was introduced into a cDNA encoding Sabin-3, the poliovirus serotype known to be most susceptible to the WIN-51711 (FIGS. 7a,b)[28].

Figure 7C:
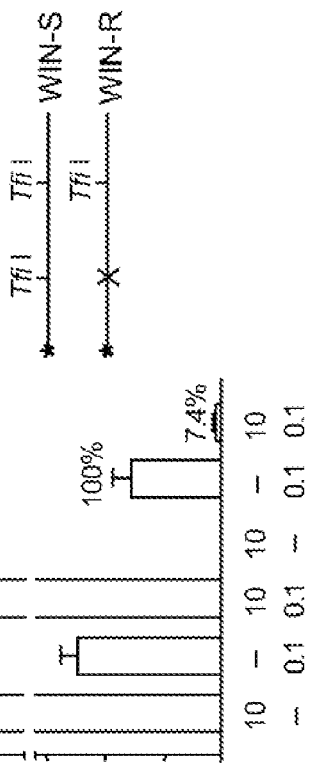
Figure 7D:
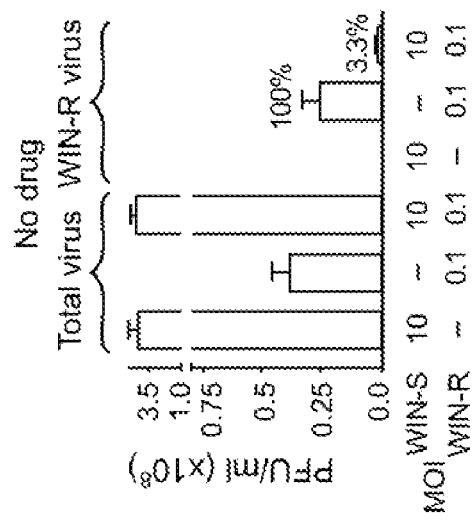
Figure 7E:
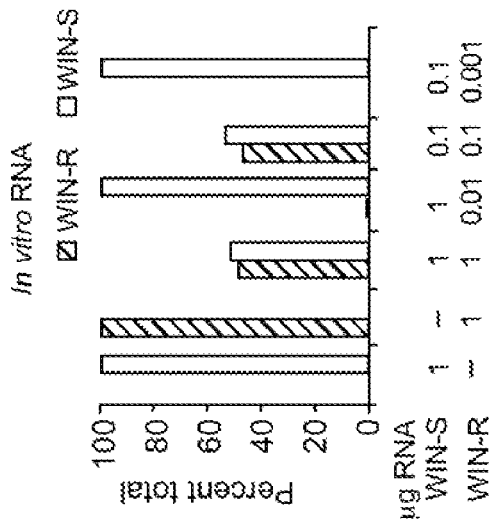

To mimic the situation in which a drug-resistant virus would appear in a cell infected with wild-type, drug-sensitive virus, co-infections of wild-type and WIN-resistant polioviruses were performed at a high multiplicity of infection (MOI) for the wild-type virus and a much lower MOI for the drug-resistant virus. As can be seen (FIGS. 7a,b), the output of WIN-resistant virus was greatly reduced when grown in the presence of drug-sensitive virus, to 7% of the yield from a single infection. The effect was similar when the single-cycle co-infections were performed in the absence or presence of the selective agent. The observed dominance of the drug-sensitive genomes may be due to chimeric capsid formation, which rendered WIN-resistant genomes susceptible to the drug, being partially encapsidated by WIN-sensitive capsid proteins. An alternative explanation, however, was that RNA replication of the WIN-resistant virus was reduced by an unknown mechanism in the co-infection. To test this possibility explicitly, total RNA from all the infections in FIG. 7a was subjected to RT-PCR. Differential digestion with a restriction enzyme was employed to determine the proportion of WIN-resistant genomes in each infection (FIGS. 7c,d). As shown in FIG. 7e, similar amounts of WIN-resistant viral RNA were present in both single and co-infections. The result argues that the reduction in WIN-resistant virus during co-infection was not due to a decrease in RNA replication, but to the formation of chimeric capsids that rendered the drug-resistant genome drug-sensitive.

FIGS. 7A-E. Co-infections of drug-sensitive and drug-resistant viruses. Viral infections were performed using either the poliovirus type-3 isolate "Fox" strain designated "WIN-S" or a WIN-51711-resistant derivative of the Sabin-3 strain containing a point mutation, VP1-I192F, labeled "WIN-R". Infections were performed singly or as co-infections, for a single round of virus growth at the indicated MOIs. After virus adsorption, virus growth continued in the absence (a) or presence (b) of 2 µg/ml WIN-51711. To measure "total virus", viral titers were determined in the absence of drug; WIN-R virus was measured by adding drug to virus stock dilutions and agar overlays. Percentages refer to the relative amounts of WIN-R virus when WIN-R virus from a single infection is defined as 100 percent with standard error measurements indicated by error bars. (c) Schematic of RT-PCR strategy used to measure ratio of WIN-S to WIN-R intracellular RNA. Total intracellular RNA was harvested after viral infection of HeLa cells grown in the absence of WIN at the MOIs indicated, subjected to RT-PCR using primers common to both WIN-S and WIN-R RNAs, and digested with a restriction enzyme, TfiI, to quantify the relative abundances of each RNA species. The asterisk (*) denotes the radiolabeled forward primer; the differential mobility of the restriction digested, radiolabeled RT-PCR product is used to distinguish WIN-R and WIN-S species in d,e. (d) Standard curve of in vitro transcribed WIN-R and WIN-S RNA. The indicated RNAs were produced from linearized cDNA templates in vitro and added to each RT-PCR reaction. The percent of total RT-PCR product that migrated as either WIN-S (white bars) or WIN-R (shaded bars) is shown for each reaction. The relative intensity of each product was quantified using a phosphorimaging plate and ImageQuant software (e) Quantitation of viral intracellular RNA from infected cells. RT-PCR reactions were performed as described in c using intracellular RNA harvested from the infections indicated in a. Each lane is labeled with the infection used in the RT-PCR reaction. "Mix" refers to a mixing of intracellular RNAs harvested from separate single infections of WIN-R and WIN-S viruses, while "co-infect." refers to the intracellular RNA harvested from a co-infection of WIN-R and WIN-S viruses. The relative mobilities of WIN-R and WIN-S digested products are indicated in the left panel. To determine the relative abundance of WIN-S and WIN-R RNA species, the indicated bands were quantified using a phosphorimaging plate and ImageQuant software. The percent of total signal for WIN-S (white bars) or WIN-R (grey bars) are indicated in the right panel graph.

REFERENCES

1. Domingo, E., and Holland, J. J. 1997. RNA virus mutations and fitness for survival. *Annu. Rev. Microbiol.* 51, 151-178 (1997).
2. Ledinko, N., and Hirst, G. K. Mixed infection of HeLa cells with polioviruses types 1 and 2. *Virology* 14, 207-219 (1961).
3. Holland, J. J., and Cords, C. E. Maturation of poliovirus RNA with capsid protein coded by heterologous enteroviruses. *Proc. Natl. Acad. Sci. USA* 51, 1082-1085 (1964).
4. Ikegami, N., Eggers, H. J., and Tamm, I. Rescue of drug-requiring and drug-inhibited enteroviruses. *Proc. Natl. Acad. Sci. USA* 52, 1419-1426 (1964).
5. Holland, J. J., de la Torre, J. C., Steinhauer, D. A., Clarke, D., Duarte, E., and Domingo, E. Virus mutation frequencies can be greatly underestimated by monoclonal antibody neutralization of virions. *J. Virol.* 63, 5030-5036 (1989).
6. Paul, A. V. 2002. Possible Unifying Mechanism of Picornavirus Genome Replication. in *Molecular Biology of Picornaviruses* (ed. B. L. Semler and E. Wimmer). pp. 227-246. ASM Press, Washington, D.C. (2002).
7. Kaplan, G. and Racaniello, V. R. Construction and characterization of poliovirus subgenomic replicons. *J. Virol.* 62, 1687-1696 (1988).
8. Novak, J. E., and Kirkegaard, K. Coupling between genome translation and replication in an RNA virus. *Genes Dev.* 8, 1726-1737 (1994).
9. Lyle, J. M., Bullitt, E., Bienz, K., Kirkegaard, K. Visualization and functional analysis of RNA-dependent RNA polymerase lattices. *Science* 296, 2218-2222 (2002).
10. Thompson, A. A., and Peersen, O. B. Structural basis for proteolysis-dependent activation of the poliovirus RNA-dependent RNA polymerase. *EMBO J.* 23, 3462-3471 (2004).
11. Paul, A. V., Rieder, E., Kim, D. W., van Boom, J. H., and Wimmer, E. Identification of an RNA hairpin in poliovirus RNA that serves as the primary template in the in vitro uridylylation of VPg. *J. Virol.* 74, 10359-10370 (2000).
12. Herskowitz, I. Functional inactivation of genes by dominant negative mutations. *Nature* 329, 219-222 (1987).
13. Yin, J., Paul, A. V., Wimmer, E., and Rieder, E. Functional dissection of a poliovirus cis-acting replication element [PV-cre(2C)]: analysis of single- and dual-cre viral genomes and proteins that bind specifically to PV-cre RNA. *J. Virol.* 77, 5152-5166 (2003).
14. Murray, K. E., and Barton, D. J. Poliovirus CRE-dependent VPg uridylylation is required for positive-strand RNA synthesis but not for negative-strand RNA synthesis. *J. Virol.* 77, 4739-4750 (2003).
15. Andino, R., Rieckhof, G. E., Achacoso, P. L., and Baltimore, D. Poliovirus RNA synthesis utilizes an RNP complex formed around the 5'-end of viral RNA. *EMBO J.* 12, 3587-3598 (1993).
16. Hambidge, S. J. and Sarnow, P. Translational enhancement of the poliovirus 5' noncoding region mediated by virus-encoded polypeptide 2A. *Proc. Natl. Acad. Sci. USA.* 89, 10272-10276 (1992).
17. Macadam, A. J., Ferguson, G., Fleming, T., Stone, D. M., Almond, J. W., and Minor, P. D. 1994. Role for poliovirus protease 2A in cap independent translation. *EMBO J.* 13, 924-927 (1994).
18. Toyoda, H., Nicklin, M. J., Murray, M. G., Anderson, C. W., Dunn, J. J., Studier, F. W., and Wimmer, E. A second virus-encoded proteinase involved in proteolytic processing of poliovirus polyprotein. *Cell* 45, 761-770 (1986).

19. Hellen, C. U., Lee, C. K., and Wimmer, E. Determinants of substrate recognition by poliovirus 2A proteinase. *J. Virol.* 66, 3330-3338 (1992).

20. Lyons, T., Murray, K. E., Roberts, A. W., and Barton, D. J. Poliovirus 5'-terminal cloverleaf RNA is required in cis for VPg uridylylation and the initiation of negative-strand RNA synthesis. *J. Virol.* 75, 10696-10708 (2001).

21. Agut, H., Kean, K. M., Fichot, O., Morasco, J., Flanegan, J. B., and Girard, M. A point mutation in the poliovirus polymerase gene determines a complementable temperature-sensitive defect of RNA replication. *Virology* 168, 302-311 (1989).

22. Charini, W. A., Burns, C. C., Ehrenfeld, E., and Semler, B. L. trans rescue of a mutant poliovirus RNA polymerase function. *J. Virol.* 65, 2655-2665 (1991).

23. Johnson, K. L., and Sarnow, P. Three poliovirus 2B mutants exhibit noncomplementable defects in viral RNA amplification and display dosage-dependent dominance over wild-type poliovirus. *J. Virol.* 65, 4341-4349 (1991).

24. Compton, S. R., Nelsen, B., and Kirkegaard, K. Temperature-sensitive poliovirus mutant fails to cleave VP0 and accumulates provirions. *J. Virol.* 64, 4067-4075 (1990).

25. Hope, D. A., Diamond, S. E., and Kirkegaard, K. Genetic dissection of interaction between poliovirus 3D polymerase and viral protein 3AB. *J. Virol.* 71, 9490-9498 (1997).

26. Fox, M. P., Otto, M. J., and McKinlay, M. A. Prevention of rhinovirus and poliovirus uncoating by WIN 51711, a new antiviral drug. *Antimicrob. Agents Chemother.* 30, 110-116 (1986).

27. Chapman, M. S., Minor, I., Rossmann, M. G., Diana, G. D., and Andries, K. Human rhinovirus 14 complexed with antiviral compound R 61837. *J. Mol. Biol.* 217, 455-463 (1991).

28. Mosser, A. G., Sgro, J. Y., and Rueckert, R. R. Distribution of drug resistance mutations in type 3 poliovirus identifies three regions involved in uncoating functions. *J. Virol.* 68, 8193-8201 (1994).

29. Pevear, D. C., Tull, T. M., Seipel M. E., and Groarke J. M. Activity of pleconaril against enteroviruses. *Antimicrob. Agents Chemother.* 43, 2109-2115 (1999).

30. Jubelt, B., Wilson, A. K., Ropka, S. L., Guidinger, P. L., and McKinlay, M. A. Clearance of a persistent human enterovirus infection of the mouse central nervous system by the antiviral agent disoxaril. *J. Infect. Dis.* 159, 866-871 (1989).

31. Groarke, J. M., and Pevear, D. C. Attenuated virulence of pleconaril-resistant coxsackievirus B3 variants. *J. Infect. Dis.* 179, 1538-1541 (1999).

32. Preugschat, F., Yao, C.-W., and Strauss, J. H. In vitro processing of Dengue virus type 2 nonstructural proteins NS2A, NS2B, and NS3. *J. Virol.* 64, 4364-4374 (1990).

33. Rost, B., and Sander, C. Conservation and prediction of solvent accessibility in protein families. *Proteins* 20, 216-226 (1994).

34. Ho, S. N., Hunt, H. D., Horton, R. M., Pullen, J. K., and Pease, L. R. Site-directed mutagenesis by overlap extension using the polymerase chain reaction. *Gene* 77, 51-59 (1989).

35. Kirkegaard, K. Mutations in VP1 of poliovirus specifically affect both encapsidation and release of viral RNA. *J. Virol.* 64, 195-206 (1990).

36. Barton, D. J., O'Donnell, B. J., and Flanegan, J. B. 5' cloverleaf in poliovirus RNA is a cis-acting replication element required for negative-strand synthesis. *EMBO J.* 20, 1439-1448 (2001).

37. Jarvis, T. C., and Kirkegaard, K. Poliovirus RNA recombination: mechanistic studies in the absence of selection. *EMBO J.* 11, 3135-3145 (1992).

38. Ansardi, D. C., and Morrow, C. D. Amino acid substitutions in the poliovirus maturation cleavage site affect assembly and result in accumulation of provirions. *J. Virol.* 69, 1540-1547 (1995).

39. Reynolds, C., Page, G., Zhou, H., and Chow, M. Identification of residues in VP2 that contribute to poliovirus neutralization antigenic site 3B. *Virology* 184, 391-396 (1991).

40. Yu, S. F., Lloyd, R. E. Identification of essential amino acid residues in the functional activity of poliovirus 2A proteinase. *Virology* 182, 615-625 (1991).

41. Rothberg, P. G., Harris, T. J., Nomoto, A., and Wimmer, E. O4-(5'-uridylyl)tyrosine is the bond between the genome-linked protein and the RNA of poliovirus. *Proc. Natl. Acad. Sci. USA* 75, 4868-4872 (1978).

42. Ambros, V., and Baltimore, D. Protein is linked to the 5' end of poliovirus RNA by a phosphodiester linkage to tyrosine. *J. Biol. Chem.* 253, 5263-5266 (1978).

43. Hammerle, T., Hellen, C. U., and Wimmer, E. Site-directed mutagenesis of the putative catalytic triad of poliovirus 3C proteinase. *J. Biol. Chem.* 266, 5412-5416 (1991).

44. Hobson, S. D., Rosenblum, E. S., Richards, O. C., Richmond, K., Kirkegaard, K., and Schultz, S. C. Oligomeric structures of poliovirus polymerase are important for function. *EMBO J.* 20, 1153-1163 (2001).

45. Hansen, J. L., Long, A. M., and Schultz, S. C. Structure of the RNA-dependent RNA polymerase of poliovirus. *Structure (London, England)* 5, 1109-1122 (1997).

46. Burns, C. C., Lawson, M. A., Semler, B. L., and Ehrenfeld, E. Effects of mutations in poliovirus 3Dpol on RNA polymerase activity and on polyprotein cleavage. *J. Virol.* 63, 4866-4874 (1989).

47. Goodfellow, I., Chaudhry, Y., Richardson, A., Meredith, J., Almond, J. W., Barclay W., Evans D. J. Identification of a cis-acting replication element within the poliovirus coding region. *J. Virol.* 74, 4590-4600 (2000).

48. Miller, S. T., Hogle, J. M. and Filman, D. J. Crystal Structure of Mahoney Strain of Poliovirus at 2.2 Å Resolution. Protein Data Bank ID: 1HXS (2001).

49. Petersen J. F., Cherney, M. M., Liebig, H. D., Skern, T., Kuechler, E., and James, M. N. The structure of the 2A proteinase from a common cold virus: a proteinase responsible for the shut-off of host-cell protein synthesis. *EMBO J.* 18, 5463-5475 (1999).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of identifying a candidate anti-viral agent, the method comprising:
   a) culturing a mammalian cell in vitro in the presence of a test agent, wherein the mammalian cell comprises:
      i) a parent RNA virus, wherein growth of the parent virus is inhibited by the test agent; and
      ii) a variant of the parent RNA virus, wherein growth of the variant RNA virus is resistant to the test agent; and
   b) determining the effect of parent virus growth on growth of the variant virus during at least one replicative cycle, wherein, when parent virus growth interferes with variant virus growth during at least one replicative cycle, the test agent is considered a candidate anti-viral agent.

2. The method of claim 1, wherein, in the presence of the candidate anti-viral agent, parent suppresses growth of any drug-resistant variant virus for at least one replicative cycle.

3. The method of claim 1, wherein the variant RNA virus genome comprises one or more changes in nucleotide sequence relative to the nucleotide sequence of the parent RNA virus, wherein the one or more changes in nucleotide sequence result in a change in the RNA and/or an encoded protein that inhibits growth of parent virus in a mammalian cell containing both parent virus and variant virus when the cell is cultured in the absence of the test agent.

4. The method of claim 3, wherein the encoded protein is an oligomeric protein.

5. The method of claim 3, wherein the encoded protein is a trans-acting protein.

6. The method of claim 1, wherein the parent and the variant RNA viruses are positive-strand RNA viruses.

7. The method of claim 1, wherein the parent and the variant RNA viruses are negative-strand RNA viruses.

8. The method of claim 1, further comprising the step of selecting for the variant of the parent RNA virus.

9. The method of claim 1, wherein the parent virus is a poliovirus, a retrovirus, or a hepatitis C virus.

10. The method of claim 4, wherein the oligomeric protein is a capsid protein, a membrane-associated protein, or a polymerase.

11. The method of claim 5, wherein the trans-acting protein is a protease that cleaves a polyprotein, a protein primer, or an RNA helicase.

* * * * *

SEQUENCE LISTING

<160> NUMBER OF SEQ ID NOS: 13

<210> SEQ ID NO 1
<211> LENGTH: 7440
<212> TYPE: DNA
<213> ORGANISM: poliovirus

<400> SEQUENCE: 1

```
ttaaaacagc tctggggttg tacccacccc agaggcccac gtggcggcta gtactccggt     60
attgcggtac ccttgtacgc ctgttttata ctcccttccc gtaacttaga cgcacaaaac    120
caagttcaat agaagggggt acaaaccagt accaccacga acaagcactt ctgtttcccc    180
ggtgatgtcg tatagactgc ttgcgtggtt gaaagcgacg gatccgttat ccgcttatgt    240
acttcgagaa gcccagtacc acctcggaat cttcgatgcg ttgcgctcag cactcaaccc    300
cagagtgtag cttaggctga tgagtctgga catccctcac cggtgacggt ggtccaggct    360
gcgttggcgg cctacctatg gctaacgcca tgggacgcta gttgtgaaca aggtgtgaag    420
agcctattga gctacataag aatcctccgg cccctgaatg cggctaatcc caacctcgga    480
gcaggtggtc acaaaccagt gattggcctg tcgtaacgcg caagtccgtg gcggaaccga    540
ctactttggg tgtccgtgtt tccttttatt ttattgtggc tgcttatggt gacaatcaca    600
gattgttatc ataaagcgaa ttggattggc catccggtga aagtgagact cattatctat    660
ctgtttgctg gatccgctcc attgagtgtg tttactctaa gtacaatttc aacagttatt    720
tcaatcagac aattgtatca taatgggtgc tcaggtttca tcacagaaag tgggcgcaca    780
tgaaaactca aatagagcgt atggtggttc taccattaat tacaccacca ttaattatta    840
tagagattca gctagtaacg cggcttcgaa acaggacttc tctcaagacc cttccaagtt    900
caccgagccc atcaaggatg tcctgataaa aacagcccca atgctaaact cgccaaacat    960
agaggcttgc gggtatagcg atagagtact gcaattaaca ctgggaaact ccactataac   1020
cacacaggag gcggctaatt cagtagtcgc ttatgggcgt tggcctgaat atctgaggga   1080
cagcgaagcc aatccagtgg accagccgac agaaccagac gtcgctgcat gcaggtttta   1140
tacgctagac accgtgtctt ggacgaaaga gtcgcgaggg tggtggtgga agttgcctga   1200
tgcactgagg gacatgggac tctttgggca aaatatgtac taccactacc taggtaggtc   1260
cgggtacacc gtgcatgtac agtgtaacgc ctccaaattc caccaggggg cactaggggt   1320
attcgccgta ccagagatgt gtctggccgg ggatagcaac accactacca tgcacaccag   1380
ctatcaaaat gccaatcctg gcgagaaagg aggcactttc acgggtacgt tcactcctga   1440
caacaaccag acatcacctg cccgcaggtt ctgcccggtg gattacctcc ttggaaatgg   1500
cacgttgttg gggaatgcct ttgtgttccc gcaccagata ataaacctac ggaccaacaa   1560
ctgtgctaca ctggtactcc cttacgtgaa ctccctctcg atagatagta tggtaaagca   1620
caataattgg ggaattgcaa tattaccatt ggccccatta aattttgcta gtgagtcctc   1680
cccagagatt ccaatcacct tgaccatagc ccctatgtgc tgtgagttca atggattaag   1740
aaacatcacc ctgccacgct tacagggcct gccggtcatg aacacccctg gtagcaatca   1800
atatcttact gcagacaact tccagtcacc gtgtgcgctg cctgaatttg atgtgacccc   1860
acctattgac atacccggtg aagtaaagaa catgatggaa ttggcagaaa tcgacaccat   1920
gattcccttt gacttaagtg ccacaaaaaa gaacaccatg gaaatgtata gggttcggtt   1980
aagtgacaaa ccacatacag acgatcccat actctgcctg tcactctctc cagcttcaga   2040
```

```
tcctaggttg tcacatacta tgcttggaga atcctaaat tactacacac actgggcagg    2100
atccctgaag ttcacgtttc tgttctgtgg attcatgatg gcaactggca aactgttggt    2160
gtcatacgcg cctcctggag ccgacccacc aaagaagcgt aaggaggcga tgttgggaac    2220
acatgtgatc tggacatag gactgcagtc ctcatgtact atggtagtgc catggattag    2280
caacaccacg tatcggcaaa ccatagatga tagtttcacc gaaggcggat acatcagcgt    2340
cttctaccaa actagaatag tcgtccctct ttcgacaccc agagagatgg acatccttgg    2400
ttttgtgtca gcgtgtaatg acttcagcgt gcgcttgttg cgagatacca cacatataga    2460
gcaaaaagcg ctagcacagg ggttaggtca gatgcttgaa agcatgattg acaacacagt    2520
ccgtgaaacg gtgggggcgg caacatctag agacgctctc ccaaacactg aagccagtgg    2580
accaacacac tccaaggaaa ttccggcact caccgcagtg gaaactgggg ccacaaatcc    2640
actagtccct tctgatacag tgcaaaccag acatgttgta caacataggt caaggtcaga    2700
gtctagcata gagtctttct tcgcgcgggg tgcatgcgtg accattatga ccgtggataa    2760
cccagcttcc accacgaata aggataagct atttgcagtg tggaagatca cttataaaga    2820
tactgtccag ttacggagga aattggagtt cttcacctat tctagatttg atatggaact    2880
tacctttgtg gttactgcaa atttcactga gactaacaat gggcatgcct taaatcaagt    2940
gtaccaaatt atgtacgtac caccaggcgc tccagtgccc gagaaatggg acgactacac    3000
atggcaaacc tcatcaaatc catcaatctt ttacacctac ggaacagctc cagcccggat    3060
ctcggtaccg tatgttggta tttcgaacgc ctattcacac ttttacgacg gttttttccaa   3120 agtaccactg aaggaccagt cggcagcact aggtgactcc ctttatggtg cagcatctct    3180
aaatgacttc ggtattttgg ctgttagagt agtcaatgat cacaacccga ccaaggtcac    3240
ctccaaaatc agagtgtatc taaaacccaa acacatcaga gtctggtgcc cgcgtccacc    3300
gagggcagtg gcgtactacg gccctggagt ggattacaag gatggtacgc ttacaccct     3360 ctccaccaag gatctgacca catatggatt cggacaccaa aacaaagcgg tgtacactgc    3420
aggttacaaa atttgcaact accacttggc cactcaggat gatttgcaaa acgcagtgaa    3480
cgtcatgtgg agtagagacc tcttagtcac agaatcaaga gcccagggca ccgattcaat    3540
cgcaaggtgc aattgcaacg caggggtgta ctactgcgag tctagaagga atactaccc     3600 agtatccttc gttggcccaa cgttccagta catggaggct aataactatt acccagctag    3660
gtaccagtcc catatgctca ttggccatgg attcgcatct ccaggggatt gtggtggcat    3720
actcagatgt caccacgggg tgatagggat cattactgct ggtggcgaag ggttggttgc    3780
attttcagac attagagact tgtatgccta cgaagaagaa gccatggaac aaggcatcac    3840
caattacata gagtcacttg gggccgcatt tggaagtgga tttactcagc agattagcga    3900
caaaataaca gagttgacca atatggtgac cagtaccatc actgaaaagc tacttaagaa    3960
cttgatcaag atcatatcct cactagttat tataactagg aactatgaag acaccacaac    4020
agtgctcgct accctggccc ttcttgggtg tgatgcttca ccatggcagt ggcttagaaa    4080
gaaagcatgc gatgttctgg agataccta tgtcatcaag caaggtgaca gttggttgaa     4140
gaagtttact gaagcatgca acgcagctaa gggactggag tgggtgtcaa acaaaatctc    4200
aaaattcatt gattggctca aggagaaaat tatcccacaa gctagagata gttggaatt     4260 tgtaacaaaa cttagacaac tagaaatgct ggaaaaccaa atctcaacta tacaccaatc    4320
atgccctagt caggaacacc aggaaattct attcaataat gtcagatggt tatccatcca    4380
```

```
gtctaagagg tttgcccctc tttacgcagt ggaagccaaa agaatacaga aactagagca    4440
tactattaac aactacatac agttcaagag caaacaccgt attgaaccag tatgtttgct    4500
agtacatggc agccccggaa caggtaaatc tgtagcaacc aacctgattg ctagagccat    4560
agctgaaaga gaaaacacgt ccacgtactc gctacccccg gatccatcac acttcgacgg    4620
atacaaacaa cagggagtgg tgattatgga cgacctgaat caaaacccag atggtgcgga    4680
catgaagctg ttctgtcaga tggtatcaac agtggagttt ataccaccca tggcatccct    4740
ggaggagaaa ggaatcctgt ttacttcaaa ttacgttcta gcatccacaa actcaagcag    4800
aatttccccc cccactgtgg cacacagtga tgcattagcc aggcgctttg cgttcgacat    4860
ggacattcag gtcatgaatg agtattctag agatgggaaa ttgaacatgg ccatggctac    4920
tgaaatgtgt aagaactgtc accaaccagc aaacttaaag agatgctgtc ctttagtgtg    4980
tggtaaggca attcaattaa tggacaaatc ttccagagtt agatacagta ttgaccagat    5040
cactacaatg attatcaatg agagaaacag aagatccaac attggcaatt gtatggaggc    5100
tttgtttcaa ggaccactcc agtataaaga cttgaaaatt gacatcaaga cgagtccccc    5160
tcctgaatgt atcaatgact tgctccaagc agttgactcc caggaggtga gagattactg    5220
tgagaagaag ggttggatag tcaacatcac cagccaggtt caaacagaaa ggaacatcaa    5280
cagggcaata acaattctac aagcggtgac aaccttcgcc gcagtggctg gagttgtcta    5340
tgtcatgtat aaactgtttg ctggacacca gggagcatac actggtttac aaacaaaaaa    5400
acccaacgtg cccaccattc ggacagcaaa ggtacaagga ccagggttcg attacgcagt    5460
ggctatggct aaaagaaaca ttgttacagc aactactagc aagggagagt tcactatgtt    5520
aggagtccac gacaacgtgg ctattttacc aacccacgct tcacctggtg aaagcattgt    5580
gatcgatggc aaagaagtgg agatcttgga tgccaaagcg ctcgaagatc aagcaggaac    5640
caatcttgaa atcactataa tcactctaaa gagaaatgaa aagttcagag acattagacc    5700
acatatacct actcaaatca ctgagacaaa tgatggagtc ttgatcgtga acactagcaa    5760
gtaccccaat atgtatgttc ctgtcggtgc tgtgactgaa cagggatatc taaatctcgg    5820
tgggcgccaa actgctcgta ctctaatgta caactttcca accagagcag gacagtgtgg    5880
tggagtcatc acatgtactg ggaaagtcat cgggatgcat gttggtggga acggttcaca    5940
cgggtttgca gcggccctga gcgatcata cttcactcag agtcaaggtg aaatccagtg    6000
gatgagacct tcgaaggaag tgggatatcc aatcataaat gccccgtcca aaaccaagct    6060
tgaacccagt gctttccact atgtgtttga aggggtgaag gaaccagcag tcctcactaa    6120
aaacgatccc aggcttaaga cagactttga ggaggcaatt ttctccaagt acgtgggtaa    6180
caaaattact gaagtggatg agtacatgaa agaggcagta gaccactatg ctggccagct    6240
catgtcacta gacatcaaca cagaacaaat gtgcttggag gatgccatgt atggcactga    6300
tggtctagaa gcacttgatt tgtccaccag tgctggctac ccttatgtag caatgggaaa    6360
gaagaagaga gacatcttga caaacaaac cagagacact aaggaaatgc aaaaactgct    6420
cgacacatat ggaatcaacc tcccactggt gacttatgta aaggatgaac ttagatccaa    6480
aacaaaggtt gagcagggga atccagatt aattgaagct tctagtttga atgactcagt    6540
ggcaatgaga atggctttg gaacctata tgctgctttt cacaaaaacc caggagtgat    6600
aacaggttca gcagtggggt gcgatccaga tttgttttgg agcaaaattc cggtattgat    6660
ggaagagaag ctgtttgctt ttgactacac agggtatgat gcatctctca gccctgcttg    6720
gttcgaggca ctaaagatgg tgcttgagaa aatcggattc ggagacagag ttgactacat    6780
```

-continued

```
cgactaccta aaccactcac accacctgta caagaataaa acatactgtg tcaagggcgg   6840
tatgccatct ggctgctcag gcacttcaat ttttaactca atgattaaca acttgattat   6900
caggacactc ttactgaaaa cctacaaggg catagattta gaccacctaa aaatgattgc   6960
ctatggtgat gatgtaattg cttcctaccc ccatgaagtt gacgctagtc tcctagccca   7020
atcaggaaaa gactatggac taactatgac tccagctgac aaatcagcta catttgaaac   7080
agtcacatgg gagaatgtaa cattcttgaa gagattcttc agggcagacg agaaataccc   7140
atttcttatt catccagtaa tgccaatgaa ggaaattcat gaatcaatta gatggactaa   7200
agatcctagg aacactcagg atcacgttcg ctctctgtgc cttttagctt ggcacaatgg   7260
cgaagaagaa tataacaaat tcctagctaa aatcaggagt gtgccaattg gaagagcttt   7320
attgctccca gagtactcaa cattgtaccg ccgttggctt gactcatttt agtaacccta   7380
cctcagtcga attggattgg gtcatactgt tgtaggggta aatttttctt taattcggag   7440
```

```

<210> SEQ ID NO 2
<211> LENGTH: 2209
<212> TYPE: PRT
<213> ORGANISM: poliovirus

<400> SEQUENCE: 2

Met Gly Ala Gln Val Ser Ser Gln Lys Val Gly Ala His Glu Asn Ser
 1               5                  10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ser Gln
        35                  40                  45

Asp Pro Ser Lys Phe Thr Glu Pro Ile Lys Asp Val Leu Ile Lys Thr
    50                  55                  60

Ala Pro Met Leu Asn Ser Pro Asn Ile Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Leu Arg
            100                 105                 110

Asp Ser Glu Ala Asn Pro Val Asp Gln Pro Thr Glu Pro Asp Val Ala
        115                 120                 125

Ala Cys Arg Phe Tyr Thr Leu Asp Thr Val Ser Trp Thr Lys Glu Ser
    130                 135                 140

Arg Gly Trp Trp Trp Lys Leu Pro Asp Ala Leu Arg Asp Met Gly Leu
145                 150                 155                 160

Phe Gly Gln Asn Met Tyr Tyr His Tyr Leu Gly Arg Ser Gly Tyr Thr
                165                 170                 175

Val His Val Gln Cys Asn Ala Ser Lys Phe His Gln Gly Ala Leu Gly
            180                 185                 190

Val Phe Ala Val Pro Glu Met Cys Leu Ala Gly Asp Ser Asn Thr Thr
        195                 200                 205

Thr Met His Thr Ser Tyr Gln Asn Ala Asn Pro Gly Glu Lys Gly Gly
    210                 215                 220

Thr Phe Thr Gly Thr Phe Thr Pro Asp Asn Asn Gln Thr Ser Pro Ala
225                 230                 235                 240

Arg Arg Phe Cys Pro Val Asp Tyr Leu Leu Gly Asn Gly Thr Leu Leu
                245                 250                 255
```

-continued

```
Gly Asn Ala Phe Val Phe Pro His Gln Ile Ile Asn Leu Arg Thr Asn
            260                 265                 270

Asn Cys Ala Thr Leu Val Leu Pro Tyr Val Asn Ser Leu Ser Ile Asp
            275                 280                 285

Ser Met Val Lys His Asn Asn Trp Gly Ile Ala Ile Leu Pro Leu Ala
            290                 295                 300

Pro Leu Asn Phe Ala Ser Glu Ser Ser Pro Glu Ile Pro Ile Thr Leu
305                 310                 315                 320

Thr Ile Ala Pro Met Cys Cys Glu Phe Asn Gly Leu Arg Asn Ile Thr
                    325                 330                 335

Leu Pro Arg Leu Gln Gly Leu Pro Val Met Asn Thr Pro Gly Ser Asn
            340                 345                 350

Gln Tyr Leu Thr Ala Asp Asn Phe Gln Ser Pro Cys Ala Leu Pro Glu
            355                 360                 365

Phe Asp Val Thr Pro Pro Ile Asp Ile Pro Gly Glu Val Lys Asn Met
    370                 375                 380

Met Glu Leu Ala Glu Ile Asp Thr Met Ile Pro Phe Asp Leu Ser Ala
385                 390                 395                 400

Thr Lys Lys Asn Thr Met Glu Met Tyr Arg Val Arg Leu Ser Asp Lys
                    405                 410                 415

Pro His Thr Asp Asp Pro Ile Leu Cys Leu Ser Leu Ser Pro Ala Ser
            420                 425                 430

Asp Pro Arg Leu Ser His Thr Met Leu Gly Glu Ile Leu Asn Tyr Tyr
            435                 440                 445

Thr His Trp Ala Gly Ser Leu Lys Phe Thr Phe Leu Phe Cys Gly Phe
    450                 455                 460

Met Met Ala Thr Gly Lys Leu Leu Val Ser Tyr Ala Pro Pro Gly Ala
465                 470                 475                 480

Asp Pro Pro Lys Lys Arg Lys Glu Ala Met Leu Gly Thr His Val Ile
                    485                 490                 495

Trp Asp Ile Gly Leu Gln Ser Ser Cys Thr Met Val Val Pro Trp Ile
            500                 505                 510

Ser Asn Thr Thr Tyr Arg Gln Thr Ile Asp Asp Ser Phe Thr Glu Gly
            515                 520                 525

Gly Tyr Ile Ser Val Phe Tyr Gln Thr Arg Ile Val Val Pro Leu Ser
    530                 535                 540

Thr Pro Arg Glu Met Asp Ile Leu Gly Phe Val Ser Ala Cys Asn Asp
545                 550                 555                 560

Phe Ser Val Arg Leu Leu Arg Asp Thr Thr His Ile Glu Gln Lys Ala
                    565                 570                 575

Leu Ala Gln Gly Leu Gly Gln Met Leu Glu Ser Met Ile Asp Asn Thr
            580                 585                 590

Val Arg Glu Thr Val Gly Ala Ala Thr Ser Arg Asp Ala Leu Pro Asn
            595                 600                 605

Thr Glu Ala Ser Gly Pro Thr His Ser Lys Glu Ile Pro Ala Leu Thr
    610                 615                 620

Ala Val Glu Thr Gly Ala Thr Asn Pro Leu Val Pro Ser Asp Thr Val
625                 630                 635                 640

Gln Thr Arg His Val Val Gln His Arg Ser Arg Ser Glu Ser Ser Ile
                    645                 650                 655

Glu Ser Phe Phe Ala Arg Gly Ala Cys Val Thr Ile Met Thr Val Asp
            660                 665                 670

Asn Pro Ala Ser Thr Thr Asn Lys Asp Lys Leu Phe Ala Val Trp Lys
```

-continued

```
                675                 680                 685
Ile Thr Tyr Lys Asp Thr Val Gln Leu Arg Arg Lys Leu Glu Phe Phe
            690                 695                 700
Thr Tyr Ser Arg Phe Asp Met Glu Leu Thr Phe Val Thr Ala Asn
705                 710                 715                 720
Phe Thr Glu Thr Asn Asn Gly His Ala Leu Asn Gln Val Tyr Gln Ile
                725                 730                 735
Met Tyr Val Pro Pro Gly Ala Pro Val Pro Glu Lys Trp Asp Asp Tyr
                740                 745                 750
Thr Trp Gln Thr Ser Ser Asn Pro Ser Ile Phe Tyr Thr Tyr Gly Thr
                755                 760                 765
Ala Pro Ala Arg Ile Ser Val Pro Tyr Val Gly Ile Ser Asn Ala Tyr
            770                 775                 780
Ser His Phe Tyr Asp Gly Phe Ser Lys Val Pro Leu Lys Asp Gln Ser
785                 790                 795                 800
Ala Ala Leu Gly Asp Ser Leu Tyr Gly Ala Ala Ser Leu Asn Asp Phe
                805                 810                 815
Gly Ile Leu Ala Val Arg Val Val Asn Asp His Asn Pro Thr Lys Val
            820                 825                 830
Thr Ser Lys Ile Arg Val Tyr Leu Lys Pro Lys His Ile Arg Val Trp
            835                 840                 845
Cys Pro Arg Pro Pro Arg Ala Val Ala Tyr Tyr Gly Pro Gly Val Asp
        850                 855                 860
Tyr Lys Asp Gly Thr Leu Thr Pro Leu Ser Thr Lys Asp Leu Thr Thr
865                 870                 875                 880
Tyr Gly Phe Gly His Gln Asn Lys Ala Val Tyr Thr Ala Gly Tyr Lys
                885                 890                 895
Ile Cys Asn Tyr His Leu Ala Thr Gln Asp Asp Leu Gln Asn Ala Val
                900                 905                 910
Asn Val Met Trp Ser Arg Asp Leu Leu Val Thr Glu Ser Arg Ala Gln
            915                 920                 925
Gly Thr Asp Ser Ile Ala Arg Cys Asn Cys Asn Ala Gly Val Tyr Tyr
        930                 935                 940
Cys Glu Ser Arg Arg Lys Tyr Tyr Pro Val Ser Phe Val Gly Pro Thr
945                 950                 955                 960
Phe Gln Tyr Met Glu Ala Asn Asn Tyr Tyr Pro Ala Arg Tyr Gln Ser
                965                 970                 975
His Met Leu Ile Gly His Gly Phe Ala Ser Pro Gly Asp Cys Gly Gly
            980                 985                 990
Ile Leu Arg Cys His His Gly Val Ile Gly Ile Ile Thr Ala Gly Gly
            995                 1000                1005
Glu Gly Leu Val Ala Phe Ser Asp Ile Arg Asp Leu Tyr Ala Tyr Glu
        1010                1015                1020
Glu Glu Ala Met Glu Gln Gly Ile Thr Asn Tyr Ile Glu Ser Leu Gly
1025                1030                1035                1040
Ala Ala Phe Gly Ser Gly Phe Thr Gln Gln Ile Ser Asp Lys Ile Thr
                1045                1050                1055
Glu Leu Thr Asn Met Val Thr Ser Thr Ile Thr Glu Lys Leu Leu Lys
            1060                1065                1070
Asn Leu Ile Lys Ile Ile Ser Ser Leu Val Ile Ile Thr Arg Asn Tyr
            1075                1080                1085
Glu Asp Thr Thr Thr Val Leu Ala Thr Leu Ala Leu Leu Gly Cys Asp
            1090                1095                1100
```

-continued

```
Ala Ser Pro Trp Gln Trp Leu Arg Lys Lys Ala Cys Asp Val Leu Glu
1105                1110                1115                1120

Ile Pro Tyr Val Ile Lys Gln Gly Asp Ser Trp Leu Lys Lys Phe Thr
            1125                1130                1135

Glu Ala Cys Asn Ala Ala Lys Gly Leu Glu Trp Val Ser Asn Lys Ile
                1140                1145                1150

Ser Lys Phe Ile Asp Trp Leu Lys Glu Lys Ile Ile Pro Gln Ala Arg
            1155                1160                1165

Asp Lys Leu Glu Phe Val Thr Lys Leu Arg Gln Leu Glu Met Leu Glu
        1170                1175                1180

Asn Gln Ile Ser Thr Ile His Gln Ser Cys Pro Ser Gln Glu His Gln
1185                1190                1195                1200

Glu Ile Leu Phe Asn Asn Val Arg Trp Leu Ser Ile Gln Ser Lys Arg
                1205                1210                1215

Phe Ala Pro Leu Tyr Ala Val Glu Ala Lys Arg Ile Gln Lys Leu Glu
                1220                1225                1230

His Thr Ile Asn Asn Tyr Ile Gln Phe Lys Ser Lys His Arg Ile Glu
        1235                1240                1245

Pro Val Cys Leu Leu Val His Gly Ser Pro Gly Thr Gly Lys Ser Val
        1250                1255                1260

Ala Thr Asn Leu Ile Ala Arg Ala Ile Ala Glu Arg Glu Asn Thr Ser
1265                1270                1275                1280

Thr Tyr Ser Leu Pro Pro Asp Pro Ser His Phe Asp Gly Tyr Lys Gln
                1285                1290                1295

Gln Gly Val Val Ile Met Asp Asp Leu Asn Gln Asn Pro Asp Gly Ala
                1300                1305                1310

Asp Met Lys Leu Phe Cys Gln Met Val Ser Thr Val Glu Phe Ile Pro
        1315                1320                1325

Pro Met Ala Ser Leu Glu Glu Lys Gly Ile Leu Phe Thr Ser Asn Tyr
        1330                1335                1340

Val Leu Ala Ser Thr Asn Ser Ser Arg Ile Ser Pro Pro Thr Val Ala
1345                1350                1355                1360

His Ser Asp Ala Leu Ala Arg Arg Phe Ala Phe Asp Met Asp Ile Gln
                1365                1370                1375

Val Met Asn Glu Tyr Ser Arg Asp Gly Lys Leu Asn Met Ala Met Ala
        1380                1385                1390

Thr Glu Met Cys Lys Asn Cys His Gln Pro Ala Asn Phe Lys Arg Cys
        1395                1400                1405

Cys Pro Leu Val Cys Gly Lys Ala Ile Gln Leu Met Asp Lys Ser Ser
    1410                1415                1420

Arg Val Arg Tyr Ser Ile Asp Gln Ile Thr Thr Met Ile Ile Asn Glu
1425                1430                1435                1440

Arg Asn Arg Arg Ser Asn Ile Gly Asn Cys Met Glu Ala Leu Phe Gln
            1445                1450                1455

Gly Pro Leu Gln Tyr Lys Asp Leu Lys Ile Asp Ile Lys Thr Ser Pro
                1460                1465                1470

Pro Pro Glu Cys Ile Asn Asp Leu Leu Gln Ala Val Asp Ser Gln Glu
        1475                1480                1485

Val Arg Asp Tyr Cys Glu Lys Lys Gly Trp Ile Val Asn Ile Thr Ser
        1490                1495                1500

Gln Val Gln Thr Glu Arg Asn Ile Asn Arg Ala Met Thr Ile Leu Gln
1505                1510                1515                1520
```

-continued

```
Ala Val Thr Thr Phe Ala Ala Val Ala Gly Val Val Tyr Val Met Tyr
            1525                1530                1535
Lys Leu Phe Ala Gly His Gln Gly Ala Tyr Thr Gly Leu Pro Asn Lys
        1540                1545                1550
Lys Pro Asn Val Pro Thr Ile Arg Thr Ala Lys Val Gln Gly Pro Gly
    1555                1560                1565
Phe Asp Tyr Ala Val Ala Met Ala Lys Arg Asn Ile Val Thr Ala Thr
1570                1575                1580
Thr Ser Lys Gly Glu Phe Thr Met Leu Gly Val His Asp Asn Val Ala
1585                1590                1595                1600
Ile Leu Pro Thr His Ala Ser Pro Gly Glu Ser Ile Val Ile Asp Gly
                1605                1610                1615
Lys Glu Val Glu Ile Leu Asp Ala Lys Ala Leu Glu Asp Gln Ala Gly
            1620                1625                1630
Thr Asn Leu Glu Ile Thr Ile Ile Thr Leu Lys Arg Asn Glu Lys Phe
        1635                1640                1645
Arg Asp Ile Arg Pro His Ile Pro Thr Gln Ile Thr Glu Thr Asn Asp
    1650                1655                1660
Gly Val Leu Ile Val Asn Thr Ser Lys Tyr Pro Asn Met Tyr Val Pro
1665                1670                1675                1680
Val Gly Ala Val Thr Glu Gln Gly Tyr Leu Asn Leu Gly Gly Arg Gln
                1685                1690                1695
Thr Ala Arg Thr Leu Met Tyr Asn Phe Pro Thr Arg Ala Gly Gln Cys
            1700                1705                1710
Gly Gly Val Ile Thr Cys Thr Gly Lys Val Ile Gly Met His Val Gly
        1715                1720                1725
Gly Asn Gly Ser His Gly Phe Ala Ala Ala Leu Lys Arg Ser Tyr Phe
    1730                1735                1740
Thr Gln Ser Gln Gly Glu Ile Gln Trp Met Arg Pro Ser Lys Glu Val
1745                1750                1755                1760
Gly Tyr Pro Ile Ile Asn Ala Pro Ser Lys Thr Lys Leu Glu Pro Ser
                1765                1770                1775
Ala Phe His Tyr Val Phe Glu Gly Val Lys Glu Pro Ala Val Leu Thr
            1780                1785                1790
Lys Asn Asp Pro Arg Leu Lys Thr Asp Phe Glu Glu Ala Ile Phe Ser
        1795                1800                1805
Lys Tyr Val Gly Asn Lys Ile Thr Glu Val Asp Glu Tyr Met Lys Glu
    1810                1815                1820
Ala Val Asp His Tyr Ala Gly Gln Leu Met Ser Leu Asp Ile Asn Thr
1825                1830                1835                1840
Glu Gln Met Cys Leu Glu Asp Ala Met Tyr Gly Thr Asp Gly Leu Glu
                1845                1850                1855
Ala Leu Asp Leu Ser Thr Ser Ala Gly Tyr Pro Tyr Val Ala Met Gly
            1860                1865                1870
Lys Lys Lys Arg Asp Ile Leu Asn Lys Gln Thr Arg Asp Thr Lys Glu
        1875                1880                1885
Met Gln Lys Leu Leu Asp Thr Tyr Gly Ile Asn Leu Pro Leu Val Thr
    1890                1895                1900
Tyr Val Lys Asp Glu Leu Arg Ser Lys Thr Lys Val Glu Gln Gly Lys
1905                1910                1915                1920
Ser Arg Leu Ile Glu Ala Ser Ser Leu Asn Asp Ser Val Ala Met Arg
                1925                1930                1935
Met Ala Phe Gly Asn Leu Tyr Ala Ala Phe His Lys Asn Pro Gly Val
```

-continued

```
            1940                1945                1950

Ile Thr Gly Ser Ala Val Gly Cys Asp Pro Asp Leu Phe Trp Ser Lys
        1955                1960                1965

Ile Pro Val Leu Met Glu Glu Lys Leu Phe Ala Phe Asp Tyr Thr Gly
    1970                1975                1980

Tyr Asp Ala Ser Leu Ser Pro Ala Trp Phe Glu Ala Leu Lys Met Val
1985                1990                1995                2000

Leu Glu Lys Ile Gly Phe Gly Asp Arg Val Asp Tyr Ile Asp Tyr Leu
                2005                2010                2015

Asn His Ser His His Leu Tyr Lys Asn Lys Thr Tyr Cys Val Lys Gly
            2020                2025                2030

Gly Met Pro Ser Gly Cys Ser Gly Thr Ser Ile Phe Asn Ser Met Ile
        2035                2040                2045

Asn Asn Leu Ile Ile Arg Thr Leu Leu Leu Lys Thr Tyr Lys Gly Ile
    2050                2055                2060

Asp Leu Asp His Leu Lys Met Ile Ala Tyr Gly Asp Asp Val Ile Ala
2065                2070                2075                2080

Ser Tyr Pro His Glu Val Asp Ala Ser Leu Leu Ala Gln Ser Gly Lys
                2085                2090                2095

Asp Tyr Gly Leu Thr Met Thr Pro Ala Asp Lys Ser Ala Thr Phe Glu
            2100                2105                2110

Thr Val Thr Trp Glu Asn Val Thr Phe Leu Lys Arg Phe Phe Arg Ala
        2115                2120                2125

Asp Glu Lys Tyr Pro Phe Leu Ile His Pro Val Met Pro Met Lys Glu
    2130                2135                2140

Ile His Glu Ser Ile Arg Trp Thr Lys Asp Pro Arg Asn Thr Gln Asp
2145                2150                2155                2160

His Val Arg Ser Leu Cys Leu Leu Ala Trp His Asn Gly Glu Glu Glu
                2165                2170                2175

Tyr Asn Lys Phe Leu Ala Lys Ile Arg Ser Val Pro Ile Gly Arg Ala
            2180                2185                2190

Leu Leu Leu Pro Glu Tyr Ser Thr Leu Tyr Arg Arg Trp Leu Asp Ser
        2195                2200                2205

Phe

<210> SEQ ID NO 3
<211> LENGTH: 272
<212> TYPE: PRT
<213> ORGANISM: poliovirus

<400> SEQUENCE: 3

Ser Pro Asn Ile Glu Ala Cys Gly Tyr Ser Asp Arg Val Leu Gln Leu
 1               5                  10                  15

Thr Leu Gly Asn Ser Thr Ile Thr Thr Gln Glu Ala Ala Asn Ser Val
            20                  25                  30

Val Ala Tyr Gly Arg Trp Pro Glu Tyr Leu Arg Asp Ser Glu Ala Asn
        35                  40                  45

Pro Val Asp Gln Pro Thr Glu Pro Asp Val Ala Ala Cys Arg Phe Tyr
    50                  55                  60

Thr Leu Asp Thr Val Ser Trp Thr Lys Glu Ser Arg Gly Trp Trp Trp
65                  70                  75                  80

Lys Leu Pro Asp Ala Leu Arg Asp Met Gly Leu Phe Gly Gln Asn Met
                85                  90                  95

Tyr Tyr His Tyr Leu Gly Arg Ser Gly Tyr Thr Val His Val Gln Cys
```

```
            100                 105                 110

Asn Ala Ser Lys Phe His Gln Gly Ala Leu Gly Val Phe Ala Val Pro
        115                 120                 125

Glu Met Cys Leu Ala Gly Asp Ser Asn Thr Thr Thr Met His Thr Ser
    130                 135                 140

Tyr Gln Asn Ala Asn Pro Gly Glu Lys Gly Gly Thr Phe Thr Gly Thr
145                 150                 155                 160

Phe Thr Pro Asp Asn Asn Gln Thr Ser Pro Ala Arg Arg Phe Cys Pro
                165                 170                 175

Val Asp Tyr Leu Leu Gly Asn Gly Thr Leu Leu Gly Asn Ala Phe Val
            180                 185                 190

Phe Pro His Gln Ile Ile Asn Leu Arg Thr Asn Asn Cys Ala Thr Leu
        195                 200                 205

Val Leu Pro Tyr Val Asn Ser Leu Ser Ile Asp Ser Met Val Lys His
    210                 215                 220

Asn Asn Trp Gly Ile Ala Ile Leu Pro Leu Ala Pro Leu Asn Phe Ala
225                 230                 235                 240

Ser Glu Ser Ser Pro Glu Ile Pro Ile Thr Leu Thr Ile Ala Pro Met
                245                 250                 255

Cys Cys Glu Phe Asn Gly Leu Arg Asn Ile Thr Leu Pro Arg Leu Gln
            260                 265                 270

<210> SEQ ID NO 4
<211> LENGTH: 238
<212> TYPE: PRT
<213> ORGANISM: poliovirus

<400> SEQUENCE: 4

Gly Leu Pro Val Met Asn Thr Pro Gly Ser Asn Gln Tyr Leu Thr Ala
 1               5                  10                  15

Asp Asn Phe Gln Ser Pro Cys Ala Leu Pro Glu Phe Asp Val Thr Pro
            20                  25                  30

Pro Ile Asp Ile Pro Gly Glu Val Lys Asn Met Met Glu Leu Ala Glu
        35                  40                  45

Ile Asp Thr Met Ile Pro Phe Asp Leu Ser Ala Thr Lys Lys Asn Thr
    50                  55                  60

Met Glu Met Tyr Arg Val Arg Leu Ser Asp Lys Pro His Thr Asp Asp
65                  70                  75                  80

Pro Ile Leu Cys Leu Ser Leu Ser Pro Ala Ser Asp Pro Arg Leu Ser
                85                  90                  95

His Thr Met Leu Gly Glu Ile Leu Asn Tyr Tyr Thr His Trp Ala Gly
            100                 105                 110

Ser Leu Lys Phe Thr Phe Leu Phe Cys Gly Phe Met Met Ala Thr Gly
        115                 120                 125

Lys Leu Leu Val Ser Tyr Ala Pro Pro Gly Ala Asp Pro Pro Lys Lys
    130                 135                 140

Arg Lys Glu Ala Met Leu Gly Thr His Val Ile Trp Asp Ile Gly Leu
145                 150                 155                 160

Gln Ser Ser Cys Thr Met Val Val Pro Trp Ile Ser Asn Thr Thr Tyr
                165                 170                 175

Arg Gln Thr Ile Asp Asp Ser Phe Thr Glu Gly Gly Tyr Ile Ser Val
            180                 185                 190

Phe Tyr Gln Thr Arg Ile Val Val Pro Leu Ser Thr Pro Arg Glu Met
        195                 200                 205
```

-continued

```
Asp Ile Leu Gly Phe Val Ser Ala Cys Asn Asp Phe Ser Val Arg Leu
    210                 215                 220

Leu Arg Asp Thr Thr His Ile Glu Gln Lys Ala Leu Ala Gln
225                 230                 235

<210> SEQ ID NO 5
<211> LENGTH: 302
<212> TYPE: PRT
<213> ORGANISM: poliovirus

<400> SEQUENCE: 5

Gly Leu Gly Gln Met Leu Glu Ser Met Ile Asp Asn Thr Val Arg Glu
 1               5                  10                  15

Thr Val Gly Ala Ala Thr Ser Arg Asp Ala Leu Pro Asn Thr Glu Ala
            20                  25                  30

Ser Gly Pro Thr His Ser Lys Glu Ile Pro Ala Leu Thr Ala Val Glu
        35                  40                  45

Thr Gly Ala Thr Asn Pro Leu Val Pro Ser Asp Thr Val Gln Thr Arg
    50                  55                  60

His Val Val Gln His Arg Ser Arg Ser Glu Ser Ser Ile Glu Ser Phe
65                  70                  75                  80

Phe Ala Arg Gly Ala Cys Val Thr Ile Met Thr Val Asp Asn Pro Ala
                85                  90                  95

Ser Thr Thr Asn Lys Asp Lys Leu Phe Ala Val Trp Lys Ile Thr Tyr
            100                 105                 110

Lys Asp Thr Val Gln Leu Arg Arg Lys Leu Glu Phe Phe Thr Tyr Ser
        115                 120                 125

Arg Phe Asp Met Glu Leu Thr Phe Val Val Thr Ala Asn Phe Thr Glu
    130                 135                 140

Thr Asn Asn Gly His Ala Leu Asn Gln Val Tyr Gln Ile Met Tyr Val
145                 150                 155                 160

Pro Pro Gly Ala Pro Val Pro Glu Lys Trp Asp Asp Tyr Thr Trp Gln
                165                 170                 175

Thr Ser Ser Asn Pro Ser Ile Phe Tyr Thr Tyr Gly Thr Ala Pro Ala
            180                 185                 190

Arg Ile Ser Val Pro Tyr Val Gly Ile Ser Asn Ala Tyr Ser His Phe
        195                 200                 205

Tyr Asp Gly Phe Ser Lys Val Pro Leu Lys Asp Gln Ser Ala Ala Leu
    210                 215                 220

Gly Asp Ser Leu Tyr Gly Ala Ala Ser Leu Asn Asp Phe Gly Ile Leu
225                 230                 235                 240

Ala Val Arg Val Val Asn Asp His Asn Pro Thr Lys Val Thr Ser Lys
                245                 250                 255

Ile Arg Val Tyr Leu Lys Pro Lys His Ile Arg Val Trp Cys Pro Arg
            260                 265                 270

Pro Pro Arg Ala Val Ala Tyr Tyr Gly Pro Gly Val Asp Tyr Lys Asp
        275                 280                 285

Gly Thr Leu Thr Pro Leu Ser Thr Lys Asp Leu Thr Thr Tyr
    290                 295                 300

<210> SEQ ID NO 6
<211> LENGTH: 149
<212> TYPE: PRT
<213> ORGANISM: poliovirus

<400> SEQUENCE: 6
```

-continued

```
Gly Phe Gly His Gln Asn Lys Ala Val Tyr Thr Ala Gly Tyr Lys Ile
 1               5                  10                  15

Cys Asn Tyr His Leu Ala Thr Gln Asp Asp Leu Gln Asn Ala Val Asn
            20                  25                  30

Val Met Trp Ser Arg Asp Leu Leu Val Thr Glu Ser Arg Ala Gln Gly
        35                  40                  45

Thr Asp Ser Ile Ala Arg Cys Asn Cys Asn Ala Gly Val Tyr Tyr Cys
    50                  55                  60

Glu Ser Arg Arg Lys Tyr Tyr Pro Val Ser Phe Val Gly Pro Thr Phe
65                  70                  75                  80

Gln Tyr Met Glu Ala Asn Asn Tyr Tyr Pro Ala Arg Tyr Gln Ser His
                85                  90                  95

Met Leu Ile Gly His Gly Phe Ala Ser Pro Gly Asp Cys Gly Gly Ile
            100                 105                 110

Leu Arg Cys His His Gly Val Ile Gly Ile Ile Thr Ala Gly Gly Glu
        115                 120                 125

Gly Leu Val Ala Phe Ser Asp Ile Arg Asp Leu Tyr Ala Tyr Glu Glu
    130                 135                 140

Glu Ala Met Glu Gln
145

<210> SEQ ID NO 7
<211> LENGTH: 97
<212> TYPE: PRT
<213> ORGANISM: poliovirus

<400> SEQUENCE: 7

Gly Ile Thr Asn Tyr Ile Glu Ser Leu Gly Ala Ala Phe Gly Ser Gly
 1               5                  10                  15

Phe Thr Gln Gln Ile Ser Asp Lys Ile Thr Glu Leu Thr Asn Met Val
            20                  25                  30

Thr Ser Thr Ile Thr Glu Lys Leu Leu Lys Asn Leu Ile Lys Ile Ile
        35                  40                  45

Ser Ser Leu Val Ile Ile Thr Arg Asn Tyr Glu Asp Thr Thr Thr Val
    50                  55                  60

Leu Ala Thr Leu Ala Leu Leu Gly Cys Asp Ala Ser Pro Trp Gln Trp
65                  70                  75                  80

Leu Arg Lys Lys Ala Cys Asp Val Leu Glu Ile Pro Tyr Val Ile Lys
                85                  90                  95

Gln

<210> SEQ ID NO 8
<211> LENGTH: 329
<212> TYPE: PRT
<213> ORGANISM: poliovirus

<400> SEQUENCE: 8

Gly Asp Ser Trp Leu Lys Lys Phe Thr Glu Ala Cys Asn Ala Ala Lys
 1               5                  10                  15

Gly Leu Glu Trp Val Ser Asn Lys Ile Ser Lys Phe Ile Asp Trp Leu
            20                  25                  30

Lys Glu Lys Ile Ile Pro Gln Ala Arg Asp Lys Leu Glu Phe Val Thr
        35                  40                  45

Lys Leu Arg Gln Leu Glu Met Leu Glu Asn Gln Ile Ser Thr Ile His
    50                  55                  60

Gln Ser Cys Pro Ser Gln Glu His Gln Glu Ile Leu Phe Asn Asn Val
```

-continued

```
                65                  70                  75                  80
Arg Trp Leu Ser Ile Gln Ser Lys Arg Phe Ala Pro Leu Tyr Ala Val
                        85                  90                  95
Glu Ala Lys Arg Ile Gln Lys Leu Glu His Thr Ile Asn Asn Tyr Ile
                100                 105                 110
Gln Phe Lys Ser Lys His Arg Ile Glu Pro Val Cys Leu Leu Val His
                115                 120                 125
Gly Ser Pro Gly Thr Gly Lys Ser Val Ala Thr Asn Leu Ile Ala Arg
        130                 135                 140
Ala Ile Ala Glu Arg Glu Asn Thr Ser Thr Tyr Ser Leu Pro Pro Asp
145                 150                 155                 160
Pro Ser His Phe Asp Gly Tyr Lys Gln Gln Gly Val Val Ile Met Asp
                165                 170                 175
Asp Leu Asn Gln Asn Pro Asp Gly Ala Asp Met Lys Leu Phe Cys Gln
                180                 185                 190
Met Val Ser Thr Val Glu Phe Ile Pro Pro Met Ala Ser Leu Glu Glu
            195                 200                 205
Lys Gly Ile Leu Phe Thr Ser Asn Tyr Val Leu Ala Ser Thr Asn Ser
    210                 215                 220
Ser Arg Ile Ser Pro Pro Thr Val Ala His Ser Asp Ala Leu Ala Arg
225                 230                 235                 240
Arg Phe Ala Phe Asp Met Asp Ile Gln Val Met Asn Glu Tyr Ser Arg
                245                 250                 255
Asp Gly Lys Leu Asn Met Ala Met Ala Thr Glu Met Cys Lys Asn Cys
                260                 265                 270
His Gln Pro Ala Asn Phe Lys Arg Cys Cys Pro Leu Val Cys Gly Lys
                275                 280                 285
Ala Ile Gln Leu Met Asp Lys Ser Ser Arg Val Arg Tyr Ser Ile Asp
            290                 295                 300
Gln Ile Thr Thr Met Ile Ile Asn Glu Arg Asn Arg Arg Ser Asn Ile
305                 310                 315                 320
Gly Asn Cys Met Glu Ala Leu Phe Gln
                325
```

<210> SEQ ID NO 9
<211> LENGTH: 87
<212> TYPE: PRT
<213> ORGANISM: poliovirus

<400> SEQUENCE: 9

```
Gly Pro Leu Gln Tyr Lys Asp Leu Lys Ile Asp Ile Lys Thr Ser Pro
1               5                   10                  15
Pro Pro Glu Cys Ile Asn Asp Leu Leu Gln Ala Val Asp Ser Gln Glu
            20                  25                  30
Val Arg Asp Tyr Cys Glu Lys Lys Gly Trp Ile Val Asn Ile Thr Ser
        35                  40                  45
Gln Val Gln Thr Glu Arg Asn Ile Asn Arg Ala Met Thr Ile Leu Gln
    50                  55                  60
Ala Val Thr Thr Phe Ala Ala Val Ala Gly Val Val Tyr Val Met Tyr
65                  70                  75                  80
Lys Leu Phe Ala Gly His Gln
                85
```

<210> SEQ ID NO 10
<211> LENGTH: 22

-continued

<212> TYPE: PRT
<213> ORGANISM: poliovirus

<400> SEQUENCE: 10

```
Gly Ala Tyr Thr Gly Leu Pro Asn Lys Lys Pro Asn Val Pro Thr Ile
 1               5                  10                  15

Arg Thr Ala Lys Val Gln
            20
```

<210> SEQ ID NO 11
<211> LENGTH: 183
<212> TYPE: PRT
<213> ORGANISM: poliovirus

<400> SEQUENCE: 11

```
Gly Pro Gly Phe Asp Tyr Ala Val Ala Met Ala Lys Arg Asn Ile Val
 1               5                  10                  15

Thr Ala Thr Thr Ser Lys Gly Glu Phe Thr Met Leu Gly Val His Asp
            20                  25                  30

Asn Val Ala Ile Leu Pro Thr His Ala Ser Pro Gly Glu Ser Ile Val
        35                  40                  45

Ile Asp Gly Lys Glu Val Glu Ile Leu Asp Ala Lys Ala Leu Glu Asp
    50                  55                  60

Gln Ala Gly Thr Asn Leu Glu Ile Thr Ile Ile Thr Leu Lys Arg Asn
65                  70                  75                  80

Glu Lys Phe Arg Asp Ile Arg Pro His Ile Pro Thr Gln Ile Thr Glu
                85                  90                  95

Thr Asn Asp Gly Val Leu Ile Val Asn Thr Ser Lys Tyr Pro Asn Met
            100                 105                 110

Tyr Val Pro Val Gly Ala Val Thr Glu Gln Gly Tyr Leu Asn Leu Gly
        115                 120                 125

Gly Arg Gln Thr Ala Arg Thr Leu Met Tyr Asn Phe Pro Thr Arg Ala
    130                 135                 140

Gly Gln Cys Gly Gly Val Ile Thr Cys Thr Gly Lys Val Ile Gly Met
145                 150                 155                 160

His Val Gly Gly Asn Gly Ser His Gly Phe Ala Ala Ala Leu Lys Arg
                165                 170                 175

Ser Tyr Phe Thr Gln Ser Gln
            180
```

<210> SEQ ID NO 12
<211> LENGTH: 461
<212> TYPE: PRT
<213> ORGANISM: poliovirus

<400> SEQUENCE: 12

```
Gly Glu Ile Gln Trp Met Arg Pro Ser Lys Glu Val Gly Tyr Pro Ile
 1               5                  10                  15

Ile Asn Ala Pro Ser Lys Thr Lys Leu Glu Pro Ser Ala Phe His Tyr
            20                  25                  30

Val Phe Glu Gly Val Lys Glu Pro Ala Val Leu Thr Lys Asn Asp Pro
        35                  40                  45

Arg Leu Lys Thr Asp Phe Glu Glu Ala Ile Phe Ser Lys Tyr Val Gly
    50                  55                  60

Asn Lys Ile Thr Glu Val Asp Glu Tyr Met Lys Glu Ala Val Asp His
65                  70                  75                  80

Tyr Ala Gly Gln Leu Met Ser Leu Asp Ile Asn Thr Glu Gln Met Cys
```

```
                  85                  90                  95
Leu Glu Asp Ala Met Tyr Gly Thr Asp Gly Leu Glu Ala Leu Asp Leu
            100                 105                 110
Ser Thr Ser Ala Gly Tyr Pro Tyr Val Ala Met Gly Lys Lys Lys Arg
            115                 120                 125
Asp Ile Leu Asn Lys Gln Thr Arg Asp Thr Lys Glu Met Gln Lys Leu
            130                 135                 140
Leu Asp Thr Tyr Gly Ile Asn Leu Pro Leu Val Thr Tyr Val Lys Asp
145                 150                 155                 160
Glu Leu Arg Ser Lys Thr Lys Val Glu Gln Gly Lys Ser Arg Leu Ile
                165                 170                 175
Glu Ala Ser Ser Leu Asn Asp Ser Val Ala Met Arg Met Ala Phe Gly
            180                 185                 190
Asn Leu Tyr Ala Ala Phe His Lys Asn Pro Gly Val Ile Thr Gly Ser
            195                 200                 205
Ala Val Gly Cys Asp Pro Asp Leu Phe Trp Ser Lys Ile Pro Val Leu
            210                 215                 220
Met Glu Glu Lys Leu Phe Ala Phe Asp Tyr Thr Gly Tyr Asp Ala Ser
225                 230                 235                 240
Leu Ser Pro Ala Trp Phe Glu Ala Leu Lys Met Val Leu Glu Lys Ile
                245                 250                 255
Gly Phe Gly Asp Arg Val Asp Tyr Ile Asp Tyr Leu Asn His Ser His
            260                 265                 270
His Leu Tyr Lys Asn Lys Thr Tyr Cys Val Lys Gly Gly Met Pro Ser
            275                 280                 285
Gly Cys Ser Gly Thr Ser Ile Phe Asn Ser Met Ile Asn Asn Leu Ile
            290                 295                 300
Ile Arg Thr Leu Leu Leu Lys Thr Tyr Lys Gly Ile Asp Leu Asp His
305                 310                 315                 320
Leu Lys Met Ile Ala Tyr Gly Asp Asp Val Ile Ala Ser Tyr Pro His
                325                 330                 335
Glu Val Asp Ala Ser Leu Leu Ala Gln Ser Gly Lys Asp Tyr Gly Leu
            340                 345                 350
Thr Met Thr Pro Ala Asp Lys Ser Ala Thr Phe Glu Thr Val Thr Trp
            355                 360                 365
Glu Asn Val Thr Phe Leu Lys Arg Phe Phe Arg Ala Asp Glu Lys Tyr
            370                 375                 380
Pro Phe Leu Ile His Pro Val Met Pro Met Lys Glu Ile His Glu Ser
385                 390                 395                 400
Ile Arg Trp Thr Lys Asp Pro Arg Asn Thr Gln Asp His Val Arg Ser
                405                 410                 415
Leu Cys Leu Leu Ala Trp His Asn Gly Glu Glu Glu Tyr Asn Lys Phe
            420                 425                 430
Leu Ala Lys Ile Arg Ser Val Pro Ile Gly Arg Ala Leu Leu Leu Pro
            435                 440                 445
Glu Tyr Ser Thr Leu Tyr Arg Arg Trp Leu Asp Ser Phe
            450                 455                 460

<210> SEQ ID NO 13
<211> LENGTH: 68
<212> TYPE: PRT
<213> ORGANISM: poliovirus

<400> SEQUENCE: 13
```

-continued

```
Gly Ala Gln Val Ser Ser Gln Lys Val Gly Ala His Glu Asn Ser Asn
 1               5                   10                  15

Arg Ala Tyr Gly Gly Ser Thr Ile Asn Tyr Thr Thr Ile Asn Tyr Tyr
            20                  25                  30

Arg Asp Ser Ala Ser Asn Ala Ala Ser Lys Gln Asp Phe Ser Gln Asp
        35                  40                  45

Pro Ser Lys Phe Thr Glu Pro Ile Lys Asp Val Leu Ile Lys Thr Ala
    50                  55                  60

Pro Met Leu Asn
65
```